(12) United States Patent
Berthon-Cedille et al.

(10) Patent No.: US 8,093,381 B2
(45) Date of Patent: Jan. 10, 2012

(54) METHOD OF SYNTHESIS OF FLUOROQUINOLONES

(75) Inventors: Laurence Berthon-Cedille, Ricquebourg (FR); Marie-Emmanuelle Leguern, Compiegne (FR); Gilles Renaud, Courbevoie (FR); Francis Tombret, Trosly-Breuil (FR)

(73) Assignee: Biocodex, Compiegne (FR)

( * ) Notice: Subject to any disclaimer, the term of this patent is extended or adjusted under 35 U.S.C. 154(b) by 90 days.

(21) Appl. No.: 12/125,434

(22) Filed: May 22, 2008

(65) Prior Publication Data

US 2009/0054643 A1 Feb. 26, 2009

(30) Foreign Application Priority Data

May 24, 2007 (FR) ..................... 07 55240

(51) Int. Cl.
*C07D 215/56* (2006.01)
*C07D 471/04* (2006.01)
*C07D 498/06* (2006.01)

(52) U.S. Cl. ............ 544/32; 544/62; 544/101; 544/128; 544/362; 544/363; 546/123; 546/156

(58) Field of Classification Search .................. None
See application file for complete search history.

(56) References Cited

U.S. PATENT DOCUMENTS

| 4,416,719 | A |  | 11/1983 | Horiuchi |
| 4,528,287 | A |  | 7/1985 | Itoh et al. |
| 5,639,886 | A |  | 6/1997 | Zerbes et al. |
| 5,723,627 | A | * | 3/1998 | Petersen et al. ............... 548/557 |

FOREIGN PATENT DOCUMENTS

| EP |  312085 | * | 4/1989 |
| GB | 2 291 421 | * | 1/1996 |
| WO | WO 03/010144 |  | 2/2003 |

OTHER PUBLICATIONS

Abaee et al. Heterocyclic Communications, vol. 11 (#5), p. 415-418 (2005).*
Bouzard D, et al, "Fluoronaphthyridines and Quinolones as Antibacterial Agents 1. Synthesis and Structure-Activity Relationships of New 1-Substituted Derivatives", Journal of Medicinal Chemistry, American Chemical Society, Washington, US, vol. 32, No. 3, 1989 pp. 537-542.

* cited by examiner

*Primary Examiner* — Emily Bernhardt
(74) *Attorney, Agent, or Firm* — B. Aaron Schulman, Esq.; Terry L. Wright, Esq.; Stites & Harbison PLLC

(57) ABSTRACT

The invention relates to a method of preparation of fluoroquinolones of formula (I) from compounds of formula (II):

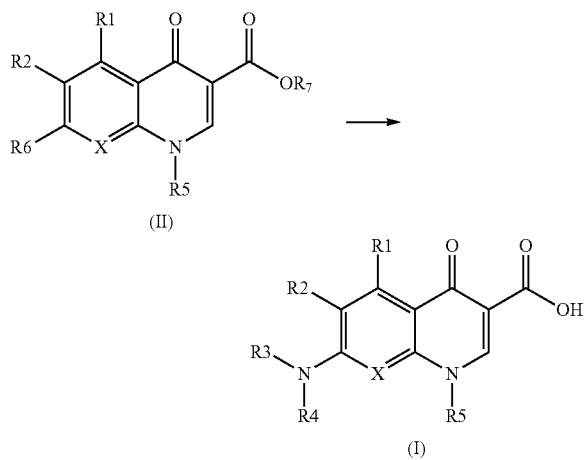

in which $R_1$, $R_2$, $R_3$, $R_4$, $R_5$, $R_6$, $R_7$, and X are as defined in Claim 1.

10 Claims, No Drawings

METHOD OF SYNTHESIS OF FLUOROQUINOLONES

TECHNICAL FIELD

The present invention relates to a method of preparation of fluoroquinolones.

BACKGROUND TO THE INVENTION

Fluoroquinolones are antibiotics obtained by chemical synthesis exhibiting a wide antibacterial spectrum. These compounds inhibit topoisomerase II or DNA gyrase and thus the replication and the transcription of the DNA of bacteria.

As examples of fluoroquinolones, mention may be made in particular of lomefloxacin, ciprofloxacin, norfloxacin and pefloxacin, the structures of which are represented below.

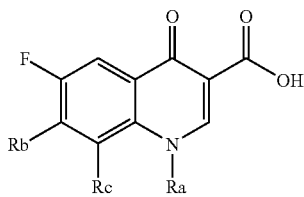

lomefloxacin: $R_a$=ethyl, $R_b$=3-methyl-1-piperazinyl, $R_c$=F; ciprofloxacin: $R_a$=cyclopropyl, $R_b$=1-piperazinyl, $R_c$=H; norfloxacin: $R_a$=ethyl, $R_b$=1-piperazinyl, $R_c$=H; pefloxacin: $R_a$=ethyl, $R_b$=4-methyl-1-piperazinyl, $R_c$=H.

Several methods of synthesis of these compounds are reported in the literature (U.S. Pat. No. 4,146,719; FR 2 555 584; Hiroshi Koga et al, *J. Med. Chem.*, 1980, 23, 1358-1363; Domagala et al, *J. Med. Chem.*, 1991, 34, 1142-1154). These methods generally involve the implementation of two steps, including in particular a step a) of carboxylic ester hydrolysis (3) into the corresponding acid (2) followed by a step b) of nucleophilic substitution of a halogen atom, in particular Cl or F, by a precursor agent of the group $R_b$, in particular a piperazinyl derivative, by which the desired fluoroquinolone (1) is obtained (Diagram I). The two chemical reactions of hydrolysis and substitution can also be implemented in reverse order, nucleophilic substitution of the halogen nucleus then hydrolysis of the ester.

Diagram I

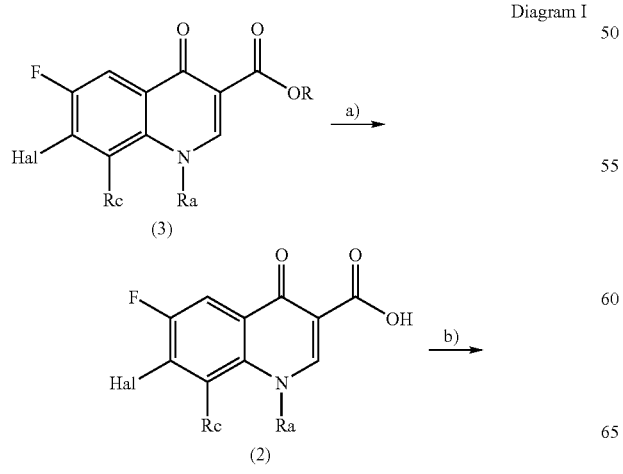

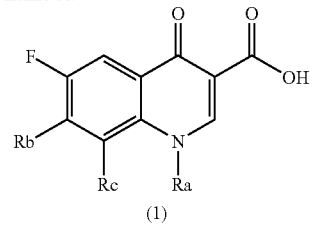

Step b) is generally carried out in the presence of an organic solvent such as pyridine or acetonitrile at reflux, or also DMF, optionally in the presence of an organic base such as triethylamine (Domagala et al, *J. Med. Chem.*, 1991, 34, 1142-1154).

A method of preparation of fluoroquinolones involving a step b) in water has recently been reported in the literature (M. Saeed Abaee et al, *Heterocyclic Communications*, Vol. 11, No. 5, 2005). However, this reaction is accompanied by the formation of a substantial quantity of position isomer. Moreover, it is necessary to heat the reaction medium for several hours at a high temperature.

A novel method has now been developed for preparation of fluoroquinolones in a limited number of steps. More specifically, according to this method, steps a) and b) above are advantageously carried out in one single step.

Moreover, this method is carried out in water which constitutes a considerable economic and ecological advantage.

Finally, this method enables access to variously substituted fluoroquinolones with high yields and a level of purity. Advantageously, the method according to the invention makes it possible to obtain yields higher than 90% and even higher than 96%.

SUMMARY OF THE INVENTION

Thus the present invention relates to a method of preparation of a compound of formula (I):

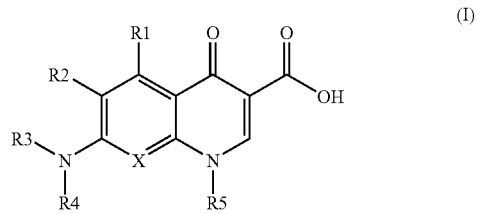

or a hydrate or an acidic or basic addition salt thereof, wherein:
$R_1$ represents a group chosen from amongst hydrogen, alkyl or NRR';
$R_2$ represents a fluorine atom;
$R_3$, $R_4$, which are identical or different,
 independently represent a hydrogen, alkyl, cycloalkyl, hydroxyl, aralkyl group, the said alkyl, cycloalkyl, aralkyl groups being capable of being optionally substituted by one or several hydroxyl groups, or NRR'; or
 form together with the nitrogen atom to which they are attached a heterocyclyl group optionally substituted by one or several groups chosen from amongst alkyl, hydroxyl, alkoxy, —C(=O)alkyl, NRR', =NOR, aralkyl, aryl, heteroaryl, the said alkyl, aryl and heteroaryl groups being capable of being optionally substituted by one or several groups chosen from amongst alkyl, halogen, perfluoroalkyl, alkoxy, NRR';

$R_5$ represents a group chosen from amongst hydrogen, alkyl, cycloalkyl, aryl, NR(CHO) or NRR', the said alkyl and aryl groups being capable of being optionally substituted by one or several groups chosen from amongst halogen or hydroxyl;

X represents a group $CR_8$ or a nitrogen atom;

$R_8$ represents a group chosen from amongst hydrogen, halogen, alkyl or alkoxy, or forms with $R_5$ a heterocyclyl group, optionally substituted by one or several alkyl groups;

R, R', which are identical or different, independently represent a hydrogen or alkyl group;

the said method comprising:

i) the reaction of a compound of formula (II)

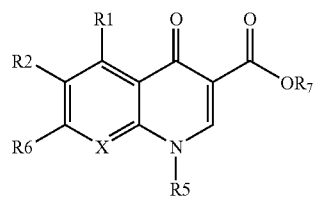

(II)

wherein $R_1$, $R_2$, $R_5$ and X are as defined above, $R_6$ represents a halogen atom, $R_7$ represents an alkyl group, with an amine of formula $R_3R_4NH$ in water; and optionally ii) the recovery of the compound of formula (I) obtained.

According to the present invention, the alkyl radicals represent saturated hydrocarbon radicals, with a straight or branched chain, having 1 to 20 carbon atoms, preferably 1 to 5 carbon atoms. When they are linear, mention may be made in particular, of methyl, ethyl, propyl, butyl, pentyl, hexyl, octyl, nonyl, decyl, dodecyl, hexadecyl and octadecyl radicals. When they are branched or substituted by one or several alkyl radicals, mention may be made in particular of isopropyl, tert-butyl, 2-ethylhexyl, 2-methylbutyl, 2-methylpentyl, 1-methylpentyl and 3-methylheptyl radicals.

The alkoxy radicals according to the present invention are radicals of formula —O-alkyl, the alkyl being as defined above.

Amongst the halogen atoms (Hal), mention may be made more particularly of fluorine, chlorine, bromine and iodine atoms, preferably chlorine or fluorine.

The cycloalkyl radical is a radical mono-, bi- or tri-cyclic saturated or partially unsaturated, non-aromatic hydrocarbon radical, having 3 to 10 carbon atoms, such as in particular cyclopropyl, cyclopentyl, cyclohexyl or adamantyl, as well as the corresponding rings containing one or several unsaturations.

Aryl designates a mono- or bicyclic aromatic hydrocarbon system, having 6 to 10 carbon atoms. Amongst the aryl radicals, mention may be made in particular the phenyl or naphthyl radical, more particularly substituted by at least one halogen atom.

Aralkyl designates an aryl-alkyl-group where aryl and alkyl are as defined above. Amongst the aralkyl radicals, mention may be made in particular of the benzyl or phenethyl radical.

The heteroaryl radicals designate the aromatic systems comprising one or several heteroatoms chosen from amongst mono- or bicyclic nitrogen, oxygen or sulphur having 5 to 10 carbon atoms. Amongst the heteroaryl radicals, mention may be made of pyrazinyl, pyrazinyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, the imidazo[2,1-b]thiazolyl, cinnolinyl, triazinyl, benzofurazanyl, azaindolyl, benzimidazolyl, benzopyrazinyl, thienopyridyl, thienopyrimidinyl, pyrrolopyridyl, imidazopyridyl, benzoazaindole, 1,2,4-triazinyl, the benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolyl, 1,3,4-thiadiazolyl, thiazolyl, triazinyl, isothiazolyl, carbazolyl, as well as condensed groups having a phenyl ring. The preferred heteroaryl groups comprise pyrazinyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolinyl, thiazolyl, carbazolyl, thiadiazolyl, and the condensed groups having a phenyl ring, and more particularly quinolynyl, carbazolyl, thiadiazolyl.

The heterocyclyl radicals designate mono- or bicyclic saturated or partially unsaturated non-aromatic systems having 5 to 10 carbon atoms, comprising one or several heteroatoms chosen from amongst N, O or S. Amongst the heterocyclyls, mention may be made in particular of oxiranyl, aziridinyl, tetrahydrofuranyl, dioxolanyl, pyrrolidinyl, pyrazolidinyl, imidazolidinyl, tetrahydrothiophenyl, dithiolanyl, thiazolidinyl, tetrahydropyranyl, dioxanyl, morpholinyl, piperidyl, piperazinyl, tetrahydrothiopyranyl, dithianyl, thiomorpholinyl, dihydrofuranyl, 2-imidazolinyl, 2,-3-pyrrolinyl, pyrazolinyl, dihydrothiophenyl, dihydropyranyl, pyranyl, tetrahydropyridyl, dihydropyridyl, tetrahydropyrimidinyl, dihydrothiopyranyl, and the corresponding groups resulting from fusion with a phenyl ring, and more particularly piperazinyl, pyrrolidinyl, piperidinyl and morpholinyl rings.

The compounds of the invention of formula (I) defined as above, having a sufficiently acid function or a sufficiently basic function or both, may include the corresponding organic or mineral acid salts or organic or mineral basic salts, preferably in pharmaceutically acceptable form. They may also be present in zwitterionic form.

The acid addition salts are formed with the useful compounds according to the invention in which a basic function such as an amino, alkylamino or dialkylamino group is present. Acid addition salts which are pharmaceutically acceptable, that is to say non-toxic, are preferred. The selected salts are chosen in an optimal manner in order to be compatible with the usual pharmaceutical vehicles and suitable for oral or parenteral administration. The acid addition salts of the compounds used according to the invention can be prepared by reaction of the free base with the appropriate acid, by the application or the adaptation of known methods. The acids suitable for use in the preparation of these salts include hydrochloric acid, hydrobromic acid, phosphoric acid, sulphuric acid, various organic carboxylic and sulphonic acids, such as acetic acid, citric acid, propionic acid, succinic acid, benzoic acid, tartaric acid, fumaric acid, mandelic acid, ascorbic acid, malic acid, methanesulphonic acid, toluenesulphonic acid, fatty acids.

The basic addition salts can be formed when the useful compound according to the invention contains a carboxyl group, or a sufficiently acid bioisoster. The bases which can be used in order to prepare the basic addition salts preferably comprise those which, when they are associated with a free acid, produce pharmaceutically acceptable salts, that is to say salts of which the cations are not toxic for the patient in pharmaceutical doses of the salts, such that the beneficial inhibiting effects inherent in the free base are not cancelled out by the secondary effects which may be attributed to the cations. The pharmaceutically acceptable salts, comprising those derived from the alkaline earth metal salts within the scope of the invention comprise those derived from the following bases: sodium, potassium hydroxide, calcium hydroxide, aluminium hydroxide, lithium hydroxide, magnesium hydroxide, zinc hydroxide, ammonia hydroxide, ethylenediamine and others.

The useful compounds according to the present invention can be easily prepared or formed during the process according to the invention, in the form of solvates (for example hydrates). The hydrates of the useful compounds according to the present invention can be easily prepared by the recrystallisation of a mixture of aqueous/organic solvents, using organic solvents such as dioxan, tetrahydrofuran or methanol.

The useful compounds of formula (II) according to the invention are those for which $R_1$ preferably represents a hydrogen atom.

$R_3$, $R_4$ preferably form together with the nitrogen atom to which they are attached a heterocyclyl group, in particular a piperazinyl, piperidinyl, pyrrolidinyl or morpholinyl group.

$R_3$, $R_4$ preferably form together with the nitrogen atom to which they are attached a piperazinyl group.

$R_5$ preferably represents an alkyl, cycloalkyl or aryl group, in particular an ethyl or cyclopropyl group or a phenyl group substituted by one or several fluorine atoms.

$R_8$ preferably represents H, F, Cl or $OCH_3$.

According to a variant, $R_8$ forms with $R_5$ a heterocyclyl group Het1:

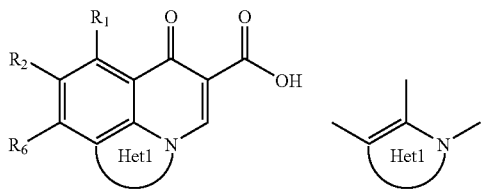

preferably represents a heterocyclyl group preferably comprising 5 to 7 links, in particular 6 links, more preferably chosen from amongst:

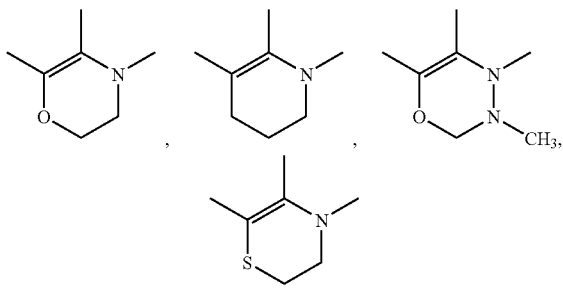

optionally substituted by one or several alkyl groups.

$R_6$ preferably represents a fluorine, chlorine or bromine atom, more preferably a fluorine atom.

More preferably, the compounds of formula (I) can be chosen from amongst:
lomefloxacin
norfloxacin
ciprofloxacin
pefloxacin
grepafloxacin or tomefloxacin
ofloxacin or levofloxacin
flerofloxacin
sarafloxacin
gatifloxacin
enrofloxacin
difloxacin
temafloxacin
amifloxacin
sitafloxacin
danofloxacin
clinafloxacin
balofloxacin
moxifloxacin
sparfloxacin
nadifloxacin
marbofloxacin
lofloxacin
rufloxacin
enofloxacin
gemifloxacin
trovafloxacin
tosufloxacin.

The amine of formula $R_3R_4NH$ implemented in step i) preferably represents 1 to 5 equivalents, more preferably 2 to 4 equivalents, in particular 3 equivalents with respect to the number of moles of the compound of formula (II). Unexpectedly, it was actually demonstrated that the use of an increasing number of equivalents of amine makes it possible to accelerate the reaction in order to achieve, on the basis of 3 equivalents, a conversion rate of more than 90% after only a few hours of reaction at temperature.

Step i) is preferably carried out in the presence of a mineral base, more preferably in the presence of an alkali metal carbonate or hydrogen carbonate, in particular $K_2CO_3$, $KHCO_3$, $Na_2CO_3$, or $NaHCO_3$, $K_2CO_3$ being particularly preferred. Advantageously, $K_2CO_3$ makes it possible to accelerate the kinetics of the reaction and leads to a very low rate of impurity.

The quantity of mineral base present in the medium is not critical. It may vary between 1.2 and 5 molar equivalents with respect to the compound of formula (II), and is preferably between 3 and 5.

The reaction may take place over a wide range of temperatures, in particular between 20° C. and 200° C. The reaction is preferably carried out at a temperature between 60° C. and 120° C., more preferably between 90° C. and 100° C.

The time required for the reaction may vary considerably, depending upon a number of factors, in particular the reaction temperature and the nature of the reagents. A duration of approximately 3 hours to approximately 12 hours is generally sufficient.

The compound thus prepared may be recovered from the reaction mixture by traditional means. For example, the compounds can be recovered either by crystallisation at controlled pH or also by addition of a solvent in which the products are not soluble, or by extraction of the reaction medium with an organic solvent which is immiscible in water, and by distilling the solvent from the extract. Moreover, the product may, if required, be further purified by various techniques, such as recrystallisation, reprecipitation or various chromatographic techniques, in particular column chromatography or preparatory thin layer chromatography.

It will be appreciated that the useful compounds according to the present invention can contain asymmetric centres. These asymmetric centres may be independently in R or S configuration. It will be apparent to the person skilled in the art that certain useful compounds according to the invention can also exhibit a geometric isomerism. It should be understood that the present invention encompasses individual geometric isomers, stereoisomers and mixtures thereof, including racemic mixtures, compounds of formula (I) above. These types of isomers can be separated from their mixtures by the application or adaptation of known methods, for example chromatographic techniques or preferential recrystallisation techniques, or they are prepared separately from appropriate isomers of their intermediates.

Moreover the method according to the invention may comprise a step subsequent to step i) or ii), in which the compound of formula (I) obtained is reacted with a hydrochloric acid solution, in such a way as to obtain the corresponding hydrochloride.

The compounds of general formula (II) are available commercially and/or can be prepared by application or adaptation of any method which is known per se and/or within the scope of the person skilled in the art, in particular those described by R. C. Larock in *Comprehensive Organic Transformations*, VCH Pub., 1989, or by application or adaptation of the methods described in the following examples.

The compounds of formula (II) can in particular be prepared from compounds of formula (III):

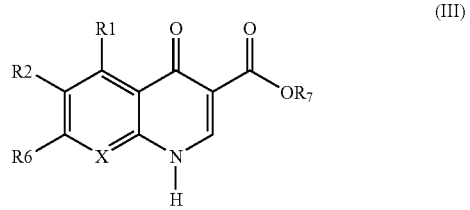

in which $R_1$, $R_2$, $R_6$, X and $R_7$ are as defined above in the general formula (II).

By way of example, a compound of formula (III) is reacted with a compound $R_5$-Hal, in the presence of an organic or mineral base such as $K_2CO_3$ or NaH, in a polar aprotic solvent such as DMF, at a temperature of approximately 100° C.

The compounds of formula (III) for which X=CR$_8$ can be prepared from compounds of formula (IV):

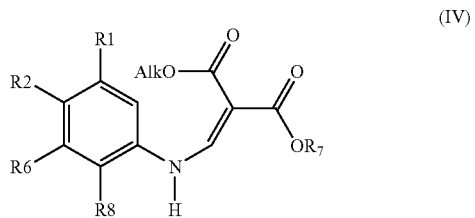

in which $R_1$, $R_2$, $R_6$, $R_8$ and $R_7$ are as defined above in the general formula (III).

By way of example, intramolecular cyclisation is carried out in Ph$_2$O by heating to a temperature of approximately 230° C.

The compounds of formula (IV) can be prepared from compounds of formula (V):

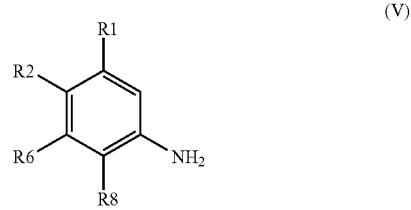

in which $R_1$, $R_2$, $R_6$ and $R_8$ are as defined in the general formula (IV).

The compounds of formula (IV) can be obtained in particular by coupling the compounds of formula (V) with of the compounds of formula (VI):

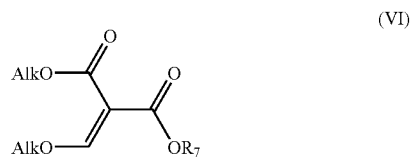

in which the Alk groups independently designate an alkyl group and $R_7$ is as defined in formula (IV). This coupling can be carried out for example in toluene at 105° C.

According to another aspect, the compounds of formula (II) can be prepared from the compounds of formula (VII):

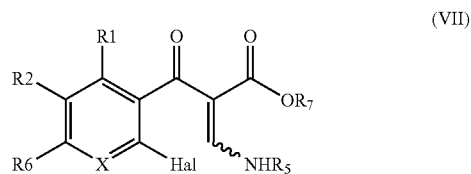

in which $R_1$, $R_2$, $R_5$, $R_6$, $R_7$ and X are as defined in the general formula (II), and Hal represents a halogen atom.

The compounds of formula (VII) can be prepared from the compounds of formula (VIII):

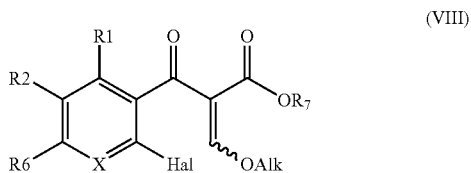

in which $R_1$, $R_2$, $R_6$, $R_7$, X and Hal are as defined in the general formula (VII) and Alk represents a alkyl group.

This step can be carried out by reacting an amine $R_5NH_2$ on a compound of formula (VIII) in a solvent such as $CH_2Cl_2$ or EtOH.

The compounds of formula (VIII) can be prepared from the compounds of formula (IX):

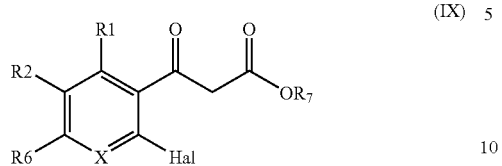

in which $R_1$, $R_2$, $R_6$, $R_7$, X and Hal are as defined in the general formula (VIII).

By way of example, this reaction can be carried out by reacting a compound $HC(OAlk)_3$ on a compound of formula (IX) in acetic anhydride.

The compounds of formula (IX) can be prepared from the compounds of formula (X):

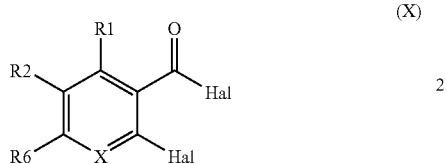

in which $R_1$, $R_2$, $R_6$ and X are as defined in the general formula (VII) and the groups Hal independently represent a halogen atom.

By way of example, this reaction can be carried out by reacting a compound of formula $R_7O(CO)CH_2COOK$ in the presence of $MgCl_2$ and of triethylamine (TEA) in acetonitrile.

Diagrams illustrating the methods of preparation of the useful compounds of formula (II) according to the invention are shown below.

Diagram II

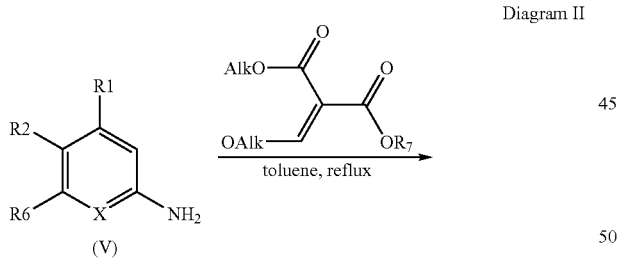

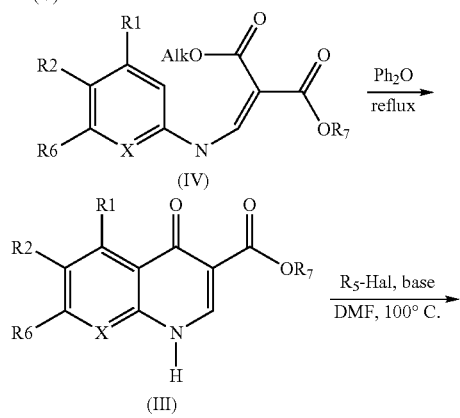

Diagram III

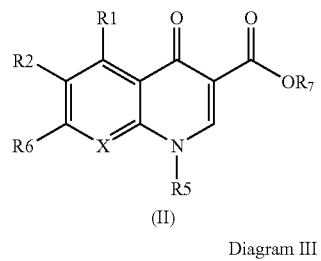

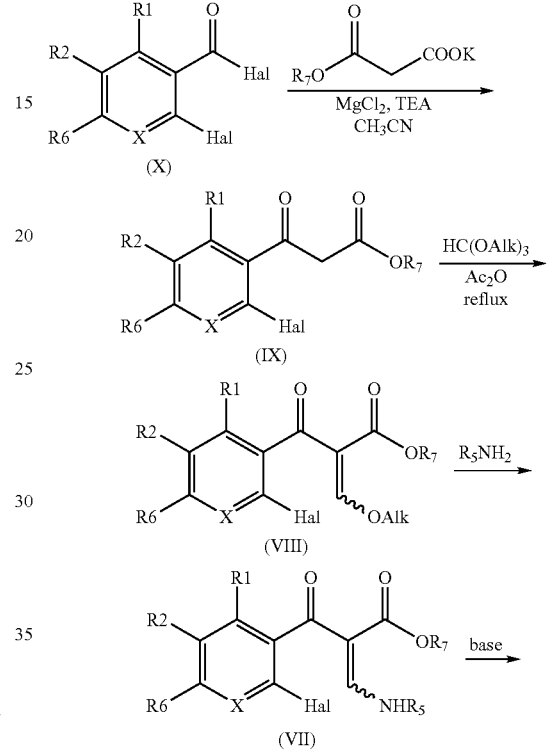

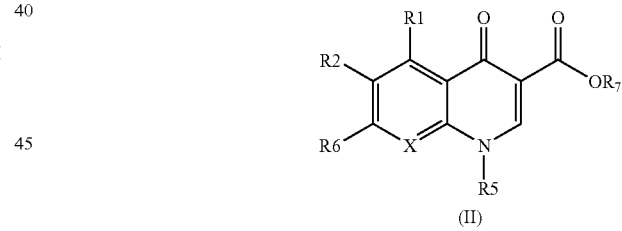

In the reactions described above, it may be necessary to protect the reactive functional groups, for example the hydroxy, amino, imino, thio, carboxy groups, when they are desired in the final product, in order to prevent them participating undesirably in the reactions. Traditional protective groups can be used in accordance with standard practice, for examples see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The basic products or the reagents used are commercially available and/or can be prepared by the application or adaptation of known methods, for example the methods as described in the examples or their obvious chemical equivalents.

DESCRIPTION OF PREFERRED EMBODIMENTS

The following examples illustrate the invention but without limiting it. The starting products used are products which are known or prepared according to known modes of operation.

The percentages are expressed by weight, unless otherwise stated.

EXAMPLES

Example 1

Method of Preparation of 1-ethyl-6,8-difluoro-1,4-dihydro-7-(3-methyl-1-piperazinyl)-4-oxoquinoline-3-carboxylic acid (lomefloxacin)

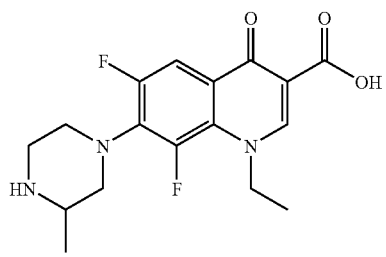

In a 1 litre three-necked flask, add 300 ml of water, stir then add 50 g of 1-ethyl-6,7,8-trifluoro-1,4-dihydro-4-oxoquinoline-3-ethyl carboxylate, 50 g of potassium carbonate and 50 g of 2-methylpiperazine. Then heat the reaction medium to 90-95° C. all together for a minimum of 10 hours, monitoring the development of the reaction by TLC. When the reaction is ended, cool the reaction medium to ambient temperature and adjust the pH to approximately 7.5 by the addition of 37% hydrochloric acid (the product is precipitated during pouring). Stir this suspension for 3 hours, readjust the pH if necessary, then dry. Make into a paste successively with 2×50 ml of water then 2×50 ml of acetone and clarify with 50 ml of acetone. After oven drying at 50° C., 56.5 g of white crystals are obtained. (Yield ~96%).

Lomefloxacin: 1-ethyl-6,8-difluoro-1,4-dihydro-7-(3-methyl-1-piperazinyl)-4-oxoquinoline-3-carboxylic acid; NR [98079-51-7].

m.p.: 238° C. [lit.: 239-240.5° C.; Merck Index 14th, 5562].

$^1$H NMR (5% NaOD/D$_2$O) in ppm: 1.07 (d; $^3$J=6.0 Hz; 3H; piperazino CH$_3$); 1.42 (t; $^3$J=6.6 Hz; 3H; ethyl CH$_3$); 2.8 to 3.1 (m; 4H; piperazino 2 CH$_2$); 3.1 to 3.4 (m; 3H; piperazino CH+piperazino CH$_2$); 4.36 (m; 2H; ethyl CH$_2$); 7.66 (dd; $^3$J$_{H-F6}$=12.6 Hz and $^5$J$_{H-F8}$=1.8 Hz; 1H; H-5); 8.32 (s; 1H; H-2).

$^{13}$C NMR (5% NaOD/D$_2$O) in ppm: 17.93 (d; $^5$J$_{C-F8}$=4.6 Hz; ethyl CH$_3$); 20.57 (s; piperazino CH$_3$); 47.51-52.89-60.00 (3 s; piperazino 3 CH$_2$); 52.70 (s; piperazino CH); 56.02 (d; $^4$J$_{C-F8}$=16.8 Hz; ethyl CH$_2$); 109.59 (d; $^2$J$_{C-F6}$=23.7 Hz; CH-5); 118.56 (s; C-3); 125.48 (d; $^2$J$_{C-F6}$=7.7 Hz; C-8a); 128.92 (d; $^3$J$_{C-F6}$=6.1 Hz; C-4a); 134.77 (t; $^2$J$_{C-F6}$~$^2$J$_{C-F8}$=14.5 Hz; C-7); 147.9 (dd; J$_{C-F8}$=248.2 Hz and J$_{C-F6}$=6.5 Hz; C-8); 152.42 (s; CH-2); 156.30 (dd; $^1$J$_{C-F6}$=245.9 Hz and $^3$J$_{C-F8}$=6.1 Hz; C-6); 174.19 (s; CO$_2$H); 176.45 (s; CO).

IR (ATR) in cm$^{-1}$: 3600 to 3200 (O—H bonded type dimer stretching and N—H secondary amine stretching), 3100 to 2800 and 2800 to 2200 (O—H acid type dimer stretching and aromatic or aliphatic C—H stretching), 3053 (aromatic C—H stretching), 1723 (C=O acid type dimer stretching), 1614 (C=O conjugated ketone stretching and asymmetrical carboxylate ion O—C—O stretching), 1475 (aromatic C=C stretching), 1338 (symmetrical carboxylate ion O—C—O stretching), 1280 (aromatic C—F stretching), 1250 (C-0 acid type dimer stretching), 930 (H—O out of plane deformation)

By way of examples, the following compounds are prepared according to the mode of operation of Example 1:

1-ethyl-6,8-difluoro-1,4-dihydro-7-[(2-hydroxypropyl)amino]-4-oxoquinoline-carboxylic acid; NR=[724737-42-2]

m.p.: 195.5° C.

$^1$H NMR (5% NaOD/D$_2$O) in ppm: 1.21 (d; $^3$J=6.2 Hz; 3H; propyl CH$_3$); 1.37 (t; $^3$J=6.6 Hz; 3H; ethyl CH$_3$); 3.2 to 3.45 (m; 2H; propyl CH$_2$); 3.85 to 4.05 (m; 1H; propyl CH); 4.15 to 4.4 (m; 2H; ethyl CH$_2$); 7.51 (dd; J$_{H-F6}$=12.8 Hz and J$_{C-F8}$=1.6 Hz; 1H; H-5); 8.26 (s; 1H; H-2).

$^{13}$C NMR (5% NaOD/D$_2$O) in ppm: 13.27 (d; $^5$J$_{C-F8}$=4.6 Hz; ethyl CH$_3$); 17.45 (s; propyl CH$_3$); 49.52 (s; propyl CH$_2$); 51.12 (d; $^4$J$_{C-F8}$ 16.8 Hz; ethyl CH$_2$); 65.16 (s; propyl CH); 104.42 (d; $^2$J$_{C-F6}$=21.4 Hz; CH-5); 113.53 (s; C-3); 115.71 (d; $^2$J$_{C-F8}$=6.9 Hz; C-8a); 124.12 (d; $^3$J$_{C-F6}$=5.4 Hz; C-4a); 128.53 (pseudo t; $^2$J$_{C-F}$=13.8 and 14.5 Hz; C-7); 136.95 (dd; $^1$J$_{C-F8}$=239.8 Hz and $^3$J$_{C-F6}$=6.9 Hz; C-8); 147.14 (s; CH-2); 147.32 (dd; $^1$J$_{C-F6}$=242.1 Hz and $^3$J$_{C-F8}$=7.7 Hz; C-6); 169.97 (s; CO$_2$H); 172.08 (s; CO).

IR (ATR) in cm$^{-1}$: 3360 (O—H bonded type dimer stretching), 3288 (N—H free secondary amine stretching), 3150 to 2800 and 2800 to 2200 (O—H acid type dimer stretching and aromatic and aliphatic C—H stretching), 1695 (C=O acid type dimer stretching), 1625 (C=O conjugated ketone stretching and asymmetrical carboxylate ion O—C—O stretching), 1488 (aromatic C=C stretching).

8-chloro-1-ethyl-6-fluoro-1,4-dihydro-7-(3-methyl-1-piperazinyl)-4-oxoquinoline-3-carboxylic acid; NR= [111234-01-6].

m.p.: 208-210° C.

$^1$H NMR (5% NaOD/D$_2$O) in ppm: 1.03 (d; $^3$J=6.0 Hz; 3H; piperazino CH$_3$); 1.33 (t; $^3$J=7.2 Hz; 3H; ethyl CH$_3$); 2.60 to 3.25 (m; 7H; piperazino CH+3 CH$_2$); 4.48 (q; $^3$J=7.0 Hz; 2H; ethyl CH$_2$); 7.68 (d; $^3$J$_{H-F}$=12.6 Hz; 1H; H-5); 8.38 (s; 1H; H-2).

$^{13}$C NMR (5% NaOD/D$_2$O) in ppm: 13.16 (s; ethyl CH$_3$); 15.93 (s; piperazino CH$_3$); 42.95-48.38-50.53-55.55 (4 s; piperazino 3 CH$_2$+ethyl CH$_2$); 48.07 (s; piperazino CH); 109.2 (d; $^2$J$_{C-F6}$=23.0 Hz; CH-5); 114.63 (s; C-3); 116.28 (s; C-8a); 123.47 (d; $^3$J$_{C-F6}$=6.8 Hz; C-4a); 133.78 (s; C-8); 140.36 (d; $^2$J$_{C-F6}$=14.5 Hz; C-7); 149.19 (s; CH-2); 153.18 (d; $^1$J$_{C-F6}$=248.0 Hz; C-6); 169.54 (s; CO$_2$H); 172.67 (s; CO).

IR (ATR) in cm$^{-1}$: 3600 to 3200 (O—H bonded type dimer stretching and N—H secondary amine stretching), 3100 to 2800 and 2800 to 2200 (O—H acid type dimer stretching and aromatic and aliphatic C—H stretching), 1725 (C=O acid type dimer stretching), 1630 to 1610 (C=O conjugated ketone stretching and asymmetrical carboxylate ion O—C—O stretching).

Norfloxacin: 1-ethyl-6-fluoro-1,4-dihydro-7-(1-piperazinyl)-4-oxoquinoline-3-carboxylic acid; NR=[70458-96-7].

m.p.: 219-220° C. [lit: 220-1° C., Merck Index 14th, 6700]

$^1$H NMR (5% NaOD/D$_2$O) in ppm: 1.39 (t; $^3$J=7.0 Hz; 3H; ethyl CH$_3$); 2 to 3.25 (m; 8H; piperazino 4 CH$_2$); 4.22

(pseudo q; $^3J$=7.0 Hz; 2H; ethyl CH$_2$); 6.88 (d; $^4J_{H\text{-}F}$=6.9 Hz; 1H; H-8); 7.79 (d; $^3J_{H\text{-}F}$=13.6 Hz; 1H; H-5); 8.37 (s; 1H; H-2).

$^{13}$C NMR (5% NaOD/D$_2$O) in ppm: 16.23 (s; ethyl CH$_3$); 46.89-53.17 (2 s; piperazino 4 CH$_2$); 51.58 (s; ethyl CH$_2$); 107.79 (s; CH-8); 114.22 (d; $^2J_{C\text{-}F6}$=22.9 Hz; CH-5); 119.32 (s; C-3); 125.07 (d; $^3J_{C\text{-}F6}$=6.9 Hz; C-4a); 138.96 (s; C-8a); 147.24 (d; $^2J_{C\text{-}F6}$=11.5 Hz; C-7); 149.47 (s; CH-2). 155.46 (d; $^1J_{C\text{-}F6}$=245.9 Hz; C-6); 175.02 (s; COOH); 177.71 (s; CO).

IR (ATR) n cm$^{-1}$: 3600 to 3200 (O—H bonded type dimer stretching and N—H secondary amine stretching), 3000 to 2800 (O—H acid type dimer stretching and aromatic and aliphatic C—H stretching), 1615 (C=O conjugated ketone stretching and asymmetrical carboxylate ion O—C—O stretching), 1484 (aromatic C=C stretching), 1331 (symmetrical carboxylate ion O—C—O stretching).

8-fluoropefloxacin: 1-ethyl-6,8-difluoro-1,4-dihydro-7-(4-methyl-1-piperazinyl)-4-oxoquinoline-3-carboxylic acid; NR=[75338-41-9].

m.p.: 235-8° C. [lit.: 240-250° C., EP 230.053 (1987)]

$^1$H NMR (CDCl$_3$) in ppm: 1.57 (t; $^3J$=7.4 Hz; 3H; ethyl CH$_3$); 2.39 (s; 3H; piperazino CH$_3$); 2.5 to 2.65 (m; 4H; piperazino CH$_2$); 3.4 to 3.5 (m; 4H; piperazino CH$_2$); 4.4 to 4.6 (m; 2H; ethyl CH$_2$); 7.93 (dd; $^3J_{H\text{-}F6}$=11.8 Hz and $^5J_{H\text{-}F8}$=1.4 Hz; 1H; H-5); 8.60 (s; 1H; H-2).

$^{13}$C NMR (CDCl$_3$) in ppm: 16.39 (d; $^5J_{C\text{-}F8}$=5.4 Hz; ethyl CH$_3$); 46.34 (s; piperazino CH$_3$); 50.87 (pseudo t; $^4J_{C\text{-}F}$~4.3 Hz; piperazino 2 CH$_2$); 55.51 (s; piperazino 2 CH$_2$); 54.68 (d; $^4J_{C\text{-}F8}$=16.8 Hz; ethyl CH$_2$); 108.25 (dd; $^2J_{C\text{-}F6}$=22.9 Hz and $^4J_{C\text{-}F8}$=3.0 Hz; CH-5); 121.08-121.27 (2 s; C-3 and C-8a); 127.31 (s; C-4a); 134.55 (t; $^2J_{C\text{-}F6}$~$^2J_{C\text{-}F8}$=14.5 Hz; C-7); 145.88 (dd; J$_{C\text{-}F8}$=247.0 Hz and J$_{C\text{-}F6}$=6.5 Hz; C-8); 150.06 (s; CH-2); 155.24 (dd; $^1J_{C\text{-}F6}$=250.1 Hz; $^3J_{C\text{-}F8}$=6.5 Hz; C-6); 166.67 (s; COOH); 176.28 (s; CO).

IR (ATR) in cm$^{-1}$: 3054 (aromatic and aliphatic C—H stretching), 3000 to 2800 (O—H acid type dimer stretching and aromatic and aliphatic C—H stretching), 1717 (C=O acid type dimer stretching), 1619 (C=O conjugated ketone stretching and asymmetrical carboxylate ion O—C—O stretching), 1470 (aromatic C=C stretching), 1281 (aromatic C—F stretching), 1243 (C—O acid type dimer stretching), 926 (H—O out of plane deformation).

1-ethyl-6,8-difluoro-1,4-dihydro-7-(4-ethyl-1-piperazinyl)-4-oxoquinoline-3-carboxylic acid; NR=[79668-41-0].

m.p.: 234-6° C. [lit.: 236-9° C., U.S. Pat. No. 4,398,029 (1983)].

$^1$H NMR (CDCl$_3$) in ppm: 1.15 (t; $^3J$=7.2 Hz; 3H; ethyl piperazino CH$_3$); 1.57 (t; $^3J$=6.8 Hz; 3H; ethyl quinolino CH$_3$); 2.52 (q; $^3J$=6.8 Hz; 2H; ethyl piperazino CH$_2$); 2.55 to 2.65 (m; 4H; piperazino 2 CH$_2$ ring); 3.4 to 3.55 (m; 4H; piperazino 2 CH$_2$ ring); 4.4 to 4.6 (m; 2H; ethyl quinolino CH$_2$); 7.95 (dd; $^3J_{H\text{-}F6}$=11.8 Hz and $^5J_{H\text{-}F8}$=2.0 Hz; 1H; H-5); 8.60 (s; 1H; H-2).

$^{13}$C NMR (CDCl$_3$) in ppm: 11.88 (s; ethyl piperazino CH$_3$); 16.35 (d; J$_{C\text{-}F8}$=4.6 Hz; ethyl quinolino CH$_3$); 50.88 (pseudo t; $^4J_{C\text{-}F}$~4.3 Hz; piperazino 2 CH$_2$ ring); 52.48 (s; CH$_2$ ethyl piperazino); 53.23 (s; piperazino 2 CH$_2$); 54.67 (d; $^4J_{C\text{-}F8}$=16.8 Hz; ethyl quinolino CH$_2$); 108.13 (dd; $^2J_{C\text{-}F6}$=22.9 Hz and $^2J_{C\text{-}F8}$=3.4 Hz; CH-5); 120.89-121.08 (2 s; C-3 and C-8a); 127.21 (s; C-4a); 134.50 (t; J$_{C\text{-}F6}$ J$_{C\text{-}F8}$=13.8 Hz; C-7); 145.78 (dd; $^1J_{C\text{-}F8}$=247.4 Hz and $^3J_{C\text{-}F6}$=6.1 Hz; C-8); 150.01 (s; CH-2); 15501 (dd; $^1J_{C\text{-}F6}$=244.7 Hz and $^3J_{C\text{-}F8}$=6.5 Hz; C-6); 166.64 (s; COOH); 176.19 (s; CO).

IR (ATR) in cm$^{-1}$: 3055 (aromatic and aliphatic C—H stretching), 3000 to 2700 (O—H acid type dimer stretching and aromatic and aliphatic C—H stretching), 1716 (C=O acid type dimer stretching), 1620 (C=O conjugated ketone stretching and asymmetrical carboxylate ion O—C—O stretching), 1470 (aromatic C=C stretching); 1286 (aromatic C—F stretching), 1241 (C—O acid type dimer stretching), 926 (H—O out of plane deformation).

1-ethyl-6,8-difluoro-1,4-dihydro-7-morpholinyl-4-oxoquinoline-3-carboxylic acid; NR=[79660-59-6].

m.p.: 260-270° C. [lit.: 268-271° C., decomp.; U.S. Pat. No. 4,398,029 (1983)].

$^1$H NMR (5% NaOD/D$_2$O) in ppm: 1.40 (t; $^3J$=6.7 Hz; 3H; ethyl CH$_3$); 3.20 to 3.40 (m; 4H; morpholino CH$_2$); 3.8 to 3.95 (m; 4H; morpholino CH$_2$); 4.20 to 4.40 (m; 2H; ethyl CH$_2$); 7.54 (d; $^3J_{H\text{-}F}$=12.8 Hz; 1H; H-5); 8.33 (s; 1H; H-2).

$^{13}$C NMR (5% NaOD/D$_2$O) in ppm: 17.91 (d; $^5J_{C\text{-}F8}$=4.6 Hz; ethyl CH$_3$); 53.39 (s; morpholino 2 CH$_2$N); 56.17 (d; $^4J_{C\text{-}F8}$=16.1 Hz; ethyl CH$_2$); 69.70 (s; morpholino 2 CH$_2$O); 109.67 (d; $^2J_{C\text{-}F6}$=22.9 Hz; CH-5); 119.01 (s; C-3); 126.18 (d; $^2J_{C\text{-}F8}$=7.7 Hz; C-8a); 129.19 (d; $^3J_{C\text{-}F6}$=7.6 Hz; C-4a); 134.46 (pseudo t; $^2J_{C\text{-}F6}$ and $^2J_{C\text{-}F8}$=13.0 and 14.5 Hz; C-7); 148.73 (dd; $^1J_{C\text{-}F8}$=249.0 Hz and $^3J_{C\text{-}F6}$=6.9 Hz; C-8); 152.26 (s; CH-2); 156.82 (dd; $^1J_{C\text{-}F6}$=246.7 Hz and $^3J_{C\text{-}F8}$=6.0 Hz; C-6); 174.53 (s; CO$_2$H); 176.65 (s; CO).

IR (ATR) in cm$^{-1}$: 3054 (aromatic and aliphatic C—H stretching), 3000 to 2800 (O—H acid type dimer stretching and aromatic and aliphatic C—H stretching), 1712 (C=O acid type dimer stretching), 1619 (C=O conjugated ketone stretching and asymmetrical carboxylate ion O—C—O stretching), 1470 (aromatic C=C stretching), 1280 (aromatic C—F stretching), 1239 (C—O acid type dimer stretching), 921 (H—O out of plane deformation)

8-fluoronorfloxacin: 1-ethyl-6,8-difluoro-1,4-dihydro-7-(piperazinyl)-4-oxoquinoline-3-carboxylic acid; NR=[99726-76-8].

m.p.: 253-4° C. [lit.: 232-6° C.; WO 8,810,253 (1988)].

$^1$H NMR (5% NaOD/D$_2$O) in ppm: 1.39 (t; $^3J$=6.6 Hz; 3H; ethyl CH$_3$); 2.85 to 3.05 (m; 4H; piperazino 2 CH$_2$ ring); 3.15 to 3.35 (m; 4H; piperazino 2 CH$_2$ ring); 4.2 to 4.45 (m; 2H; ethyl CH$_2$); 7.58 (d; $^3J_{H\text{-}F}$=12.4 Hz; 1H; H-5); 8.32 (s; 1H; H-2).

$^{13}$C NMR (5% NaOD/D$_2$O) in ppm: 18.06 (d; $^5J_{C\text{-}F8}$=4.6 Hz; ethyl CH$_3$); 47.75-53.95 (2 s; piperazino CH$_2$ ring); 56.22 (d; $^4J_{C\text{-}F8}$=16.7 Hz; ethyl CH$_2$); 109.73 (d; $^2J_{C\text{-}F6}$=22.9 Hz; CH-5); 118.77 (s; C-3); 125.78 (d; $^2J_{C\text{-}F8}$=7.7 Hz; C-8a); 129.09 (d; $^3J_{C\text{-}F6}$=6.9 Hz; C-4a); 135.11 (t; $^2J_{C\text{-}F6}$~$^2J_{C\text{-}F8}$=13.8 Hz; C-7); 148.35 (dd; $^1J_{C\text{-}F8}$=248.2 Hz and $^3J_{C\text{-}F6}$=5.7 Hz; C-8); 152.52 (s; CH-2); 156.62 (dd; $^1J_{C\text{-}F6}$=246.6 Hz and $^3J_{C\text{-}F8}$=5.7 Hz; C-6); 174.40 (s; COOH); 176.62 (s; CO).

IR (ATR) in cm$^{-1}$: 3600 to 3200 (O—H bonded type dimer stretching and N—H secondary amine stretching), 3100 to 2800 and 2800 to 2200 (O—H acid type dimer stretching and aromatic or aliphatic C—H stretching), 3033 (aromatic C—H stretching), 1634 (C=O acid type dimer stretching), 1616 (C=O conjugated ketone stretching and asymmetrical carboxylate ion O—C—O stretching), 1473 (aromatic C=C stretching), 1279 (aromatic C—F stretching), 944 (H—O out of plane deformation).

Sparfloxacin: 5-amino-1-cyclopropyl-7-[(3R,5S)-3,5-dimethyl-1-piperazinyl]-6,8-difluoro-1,4-dihydro-4-oxo-quinoline-3-carboxylic acid (relative stereochemistry); NR (x HCl)=[127585-83-5].

m.p.: >285° C. (x HCl). [lit.: 266-9° C. (base); Merck Index 14th, 8735]

$^1$H NMR (5% NaOD/D$_2$O) in ppm: 0.85 to 1.0 (m; 2H; cyclopropyl CH$_2$); 1.04 (d; $^3$J=6.3 Hz; 6H; piperazino 2 CH$_3$); 1.0 to 1.20 (m; 2H; cyclopropyl CH$_2$); 2.65 to 3.0 (2 m; 4H; piperazino 2 CH and 1 CH$_2$); 3.1 to 3.3 (d wide; 2H; CH$_2$ piperazino); 3.65 to 3.8 (m; 1H; cyclopropyl CH); 8.27 (s; 1H; H-2).

$^{13}$C NMR (5% NaOD/D$_2$O) in ppm: 11.0 (s; cyclopropyl CH$_2$); 20.6 (s; piperazino 2 CH$_3$); 41.89 (d; $^4$J$_{C-F8}$=15.0 Hz; cyclopropyl CH); 53.14 (s; piperazino 2 CH); 59.54 (s; piperazino 2 CH$_2$); 111.49 (d; $^3$J$_{C-F6}$=4.6 Hz; C-4a); 117.99 (s; C-3); 130.62 (d; $^2$J$_{C-F6}$=6.0 Hz; C-5); 134.81 (pseudo t; $^2$J$_{C-F}$=11.5 and 12.95 Hz; C-7); 137.47 (d, $^2$J$_{C-F8}$=12.3 Hz; C-8a); 138.82 (dd; $^1$J$_{C-F8}$=235.9 Hz and $^3$J$_{C-F6}$=5.5 Hz; C-8); 142.20 (dd; $^1$J$_{C-F6}$=234.4 Hz and $^3$J$_{C-F8}$=5.5 Hz; C-6); 151.19 (s; CH-2); 174.51 (s; CO$_2$H); 181.64 (s; CO).

IR (ATR) in cm$^{-1}$: 3412 (O—H bonded type dimer stretching and N—H secondary amine stretching), 3272 (N—H primary bonded stretching), 3200 to 2800 and 2800 to 2200 (O—H acid type dimer stretching and aromatic or aliphatic C—H stretching), 1711 (C=O acid type dimer stretching), 1632 (C=O conjugated ketone stretching), 1514 (asymmetrical carboxylate ion O—C—O stretching and vibration of primary N—H deformation), 1435 (aromatic C=C stretching), 1295 (aromatic C—F stretching).

1-ethyl-6,8-difluoro-1,4-dihydro-7-(4-(2-methoxyphenyl)-1-piperazinyl)-4-oxoquinoline-3-carboxylic acid; NR=[153468-44-1]

m.p.: 217-8° C., decomposition.

$^1$H NMR (CDCl$_3$) in ppm: 1.58 (t; $^3$J=6.9 Hz; 3H; ethyl CH$_3$); 3.1 to 3.35 (m; 4H; piperazino 2 CH$_2$ ring); 3.5 to 3.7 (m; 4H; piperazino 2 CH$_2$ ring); 3.91 (s; 3H; methoxy CH$_3$); 4.4 to 4.6 (m; 2H; ethyl CH$_2$); 6.8 to 7.1 (m; 4H; aromatic H); 7.93 (dd; $^3$J$_{H-F}$=11.8 Hz and J$_{H-F}$=1.4 Hz; 1H; H-5); 8.61 (s; 1H; H-8); 14.7 (s wide; COOH).

$^{13}$C NMR (CDCl$_3$) in ppm: 16.37 (d; $^5$J$_{C-F8}$=4.6 Hz; ethyl CH$_3$); 51.26 to 51.35 (2 s; piperazino 4 CH$_2$ ring); 54.63 (d; $^4$J$_{C-F8}$=16.8 Hz; ethyl CH$_2$); 55.48 (s; methoxy CH$_3$); 107.91 (s; C-3); 108.20 (dd; $^2$J$_{C-F6}$=23.7 Hz and $^4$J$_{C-F8}$=3.1 Hz; CH-5); 111.38-118.29-121.06-123.41 (4 s; 2-methoxyphenyl 4 CH nucleus); 121.23 (s; C-8a); 127.21 (d; $^3$J$_{C-F6}$=6.9 Hz; C-4-a); 134.58 (pseudo t; $^2$J$_{C-F}$=13.0 Hz and $^2$J$_{C-F}$=14.6 Hz; C-7); 141.04 (s; C-1'); 145.92 (dd; $^1$J$_{C-F8}$=247.4 Hz and $^3$J$_{C-F6}$=6.5 Hz; C-8); 150.11 (s; CH-2); 152.30 (s; C-2'); 155.18 (dd; $^1$J$_{C-F6}$=250.5 Hz and $^3$J$_{C-F8}$=6.5 Hz; C-6); 166.63 (s; CO$_2$H); 176.22 (CO).

IR (ATR) in cm$^{-1}$: 3055 (aromatic and aliphatic C—H stretching), 3000 to 2750 (O—H acid type dimer stretching and aromatic and aliphatic C—H stretching), 1718 (C=O acid type dimer stretching), 1622 (C=O conjugated ketone stretching and asymmetrical carboxylate ion O—C—O stretching), 1473 (aromatic C=C stretching), 1282 (aromatic C—F stretching), 1239 (C—O acid type dimer stretching), 927 (H—O out of plane deformation)

1-ethyl-6,8-difluoro-1,4-dihydro-7-(4-hydroxypiperidino)-4-oxoquinoline-3-carboxylic acid; NR=[79666-56-3].

m.p.: 211° C. [lit.: 216-8° C.; U.S. Pat. No. 4,398,029 (1983)].

$^1$H NMR (5% NaOD/D$_2$O) in ppm: 1.39 (t wide; $^3$J=7.0 Hz; 3H; ethyl CH$_3$); 1.5 to 1.8 (m; 2H; piperidino CH$_2$); 1.90 to 2.1 (m; 2H; piperidino CH$_2$); 3.05 to 3.15 (m; 2H; piperidino CH$_2$); 3.3 to 3.5 (m; 2H; piperidino CH$_2$); 3.85 (m; 1H; piperidino CH); 4.31 (m; 2H; ethyl CH$_2$); 7.60 (d; $^3$J$_{H-F}$=12.2 Hz; 1H; H-5); 8.31 (s; 1H; H-2).

$^{13}$C NMR (5% NaOD/D$_2$O) in ppm: 18.07 (d; $^5$J$_{C-F8}$=5.0 Hz; ethyl CH$_3$); 36.68 (s; piperidino 2 CH$_2$); 51.66 (s; piperidino CH$_2$—N); 56.30 (d; $^4$J$_{C-F8}$=16.8 Hz; ethyl CH$_2$); 57.05 (s; piperidino CH$_2$—N); 69.97 (s; piperidino CH); 109.76 (d; $^2$J$_{C-F6}$=22.2 Hz; CH-5); 119.02 (s; C-3); 125.89 (d; $^3$J$_{C-F6}$=6.9 Hz; C-4a); 129.32 (d; $^2$J$_{C-F8}$=7.7 Hz; C-8a); 135.46 (pseudo t; $^2$J$_{C-F6}$~$^2$J$_{C-F8}$=13.7 Hz; C-7); 148.72 (dd; J$_{C-F8}$=248.5 Hz; $^3$J$_{C-F6}$=6.5 Hz; C-8); 152.40 (s; CH-2); 156.99 (dd; $^1$J$_{C-F6}$=244.5 Hz and $^3$J$_{C-F8}$=6.0 Hz; C-6); 174.66 (s; COOH); 176.83 (s; CO).

IR (ATR) in cm$^{-1}$: 3500 to 3150 (O—H bonded type dimer stretching), 3050 (aromatic and aliphatic C—H stretching), 3000 to 2800 and 2800 to 2200 (aromatic and aliphatic C—H stretching), 1716 (C=O acid type dimer stretching), 1620 (C=O conjugated ketone stretching and asymmetrical carboxylate ion O—C—O stretching), 1464 (aromatic C=C stretching), 1280 (aromatic C—F stretching), 926 (H—O out of plane deformation).

Flerofloxacin: 1-(2-fluoro-1-ethyl)-6,8-difluoro-1,4-dihydro-7-(4-methyl-1-piperazinyl)-4-oxoquinoline-3-carboxylic acid; NR=[79660-72-3].

m.p.: 271-3° C.

$^1$H NMR (5% NaOD/D$_2$O) in ppm: 2.30 (s; 3H; piperazino CH$_3$); 2.4 to 2.75 (m; 4H; piperazino 2 CH$_2$); 3.2 to 3.5 (m; 4H; piperazino 2 CH$_2$); 4.5 to 5.1 (m; 4H; fluoroethyl 2 CH$_2$); 7.68 (d; $^3$J$_{H-F}$=12.6 Hz; 1H; H-5); 8.29 (s; 1H; H-2).

$^{13}$C NMR (5% NaOD/D$_2$O) in ppm: 42.73 (s; piperazino CH$_3$); 48.02-52.28 (2 s; piperazino 4 CH$_2$); 55.65 (d, $^2$J$_{C-F}$=19.1 Hz; N1-CH$_2$); 80.52 (d; $^1$J$_{C-F}$=164.9 Hz; CH$_2$—F); 105.26 (d; $^2$J$_{C-F6}$=24.5 Hz; CH-5); 114.41 (s; C-3); 121.24 (d; $^2$J$_{C-F8}$=8.5 Hz; C-8a); 124.57 (d; $^3$J$_{C-F6}$=7.5 Hz; C-4a); 130.29 (t; $^2$J$_{C-F}$=14.0 Hz; C-7); 144.07 (dd; $^1$J$_{C-F8}$=246.0 Hz and $^3$J$_{C-F6}$=6.0 Hz, C-8); 148.52 (s; CH-2); 152.13 (dd; $^1$J$_{C-F6}$=244.5 Hz and $^3$J$_{C-F8}$=6.5 Hz; C-6); 169.67 (s; CO$_2$H); 172.28 (s; CO).

IR (ATR) in cm$^{-1}$: 3050 (aromatic and aliphatic C—H stretching), 3000 to 2700 (O—H acid type dimer stretching and aromatic and aliphatic C—H stretching), 1716 (C=O acid type dimer stretching), 1625 (C=O conjugated ketone stretching and asymmetrical carboxylate ion O—C—O stretching), 1476 (aromatic C=C stretching), 1281 (aromatic C—F stretching), 926 (H—O out of plane deformation).

Enofloxacin: 1-ethyl-6-fluoro-1,4-dihydro-4-oxo-7-(1-piperazinyl)-1,8-naphthyridine-3-carboxylic acid; NR=[74011-58-8].

m.p.: 220° C. [lit. 220-4° C.; Merck index 14th, 3587]

$^1$H NMR (DMSO-d6) in ppm: 1.42 (t; $^3$J=7.0 Hz; 3H; ethyl CH$_3$); 2.7 to 3.0 (m; 4H; piperazino 2 CH$_2$); 3.7 to 3.9 (m; 4H; piperazino 2 CH$_2$); 4.52 (q wide; $^3$J=7.0 Hz; 2H; ethyl CH$_2$); 8.09 (d; $^3$J$_{H-F}$=14.2 Hz; 1H; H-5); 9.01 (s; 1H; H-2).

$^{13}$C NMR (5% NaOD/D$_2$O) in ppm: 16.78 (s; ethyl CH$_3$); 47.17 (s; piperazino 2 CH$_2$); 49.66-49.98-50.13 (3 s; piperazino 2 CH$_2$ and ethyl CH$_2$); 117.33 (d; $^4$J$_{C-F6}$=3.9 Hz; C-4a); 120.44 (s; C-3); 122.22 (d; $^2$J$_{C-F6}$=21.4 Hz; CH-5); 146.84 (s; C-8a); 148.28 (s; CH-2); 149.48 (d; $^1$J$_{C-F6}$=256.6 Hz; C-6); 152.35 (d; $^2$J$_{C-F}$=9.2 Hz; C-7); 175.12 (s; CO$_2$H); 178.22 (s; CO).

IR (ATR) in cm$^{-1}$: 3050 (aromatic and aliphatic C—H stretching), 3000 to 2800 (O—H acid type dimer stretching and aromatic and aliphatic C—H stretching), 1713 (C=O acid type dimer stretching), 1623 (C=O conjugated ketone stretching and asymmetrical carboxylate ion O—C—O stretching), 1475 (aromatic C=C stretching), 1287 (aromatic C—F stretching C—F), 950 (H—O out of plane deformation).

Temafloxacin: 1-(2,4-difluorophenyl)-6-fluoro-1,4-dihydro-7-(3-methyl-1-piperazinyl)-4-oxoquinoline-3-carboxylic acid; NR=[108319-06-8].

m.p.: 125-130° C., decomposition.

$^1$H NMR (5% NaOD/D$_2$O) in ppm: 0.99 (d; $^3$J=6.2 Hz; 3H; piperazino CH$_3$); 2.24 (t, J=11.1 Hz; 1H; piperazino CH$_2$H); 2.57 (t wide; J=10.6 Hz; 1H; piperazino CH$_2$H); 2.70 to 3.0 (m; 3H; piperazino CH$_2$H); 3.2 to 3.4 (m; 2H; piperazino CH$_2$); 6.39 (d; $^4$J$_{H-F}$=7.0 Hz; 1H; H-8); 7.2 to 7.4 (m; aromatic 2H); 7.55 to 7.7 (m; aromatic 1H); 7.90 (d; $^3$J$_{H-F}$=13.2 Hz; 1H; H-5); 8.37 (s; 1H; H-2).

$^{13}$C NMR (5% NaOD/D$_2$O) in ppm: 16.00 (s; piperazino CH$_3$); 41.90 (s; piperazino 2 CH$_2$); 47.26 (s; piperazino CH); 54.25 (s; piperazino CH$_2$); 103.56 (s; C-8); 109.65 (d; $^2$J$_{C-F}$=22.5 Hz; aromatic CH-5 or CH-3'); 111.18 (d; $^2$J$_{C-F}$=22.5 Hz; aromatic CH-3' or CH-5'); 115.96 (s; C-3); 119.32 (d; $^3$J$_{C-F6}$=7.6 Hz; C-4a); 121.83 (d; $^2$J$_{C-F}$=13.0 Hz; aromatic C-1'); 128.3-128.42 (2 s; aromatic CH-5' and CH-6'); 136.01 (s; C-8a); 142.61 (d; $^2$J$_{C-F6}$=10.7 Hz; C-7); 145.02 (s; CH-2); 150.99 (d; $^1$J$_{C-F6}$=247.5 Hz; C-6); 155.29 (dd; $^1$J$_{C-F}$=252.5 Hz and $^3$J$_{C-F}$=15.5 Hz; aromatic C-2' or C-4'); 161.19 (dd; $^1$J$_{C-F}$=249.5 Hz and $^3$J$_{C-F}$=12 Hz; aromatic C-2' or C-4'); 169.83 (s; CO$_2$H); 17384 (s; CO).

IR (ATR) in cm$^{-1}$: 3600 to 3200 (bonded dimer type stretching and N—H secondary amine stretching), 3020 (aromatic and aliphatic C—H stretching), 3000 to 2800 and 2800 to 2200 (acid type dimer stretching and aromatic and aliphatic C—H stretching), 1626 (C=O conjugated ketone stretching and asymmetrical carboxylate ion O—C—O stretching), 1470 (aromatic C=F stretching), 1286 (aromatic C—F stretching).

Difloxacin: 1-(4-fluorophenyl)-6-fluoro-1,4-dihydro-7-(4-methyl-1-piperazinyl)-4-oxoquinoline-3-carboxylic acid; NR=[98106-17-3].

m.p.: 260-265° C.

$^1$H NMR (CDCl$_3$) in ppm: 2.33 (s; 3H; piperazino CH$_3$); 2.5 to 2.6 (m; 4H; piperazino CH$_2$); 3.05 to 3.2 (m; 4H; piperazino CH$_2$); 6.8 (d; $^4$J$_{H-F6}$=7.2 Hz; 1H; H-8); 7.25 to 7.50 (m; aromatic 4H); 8.05 (d; $^3$J$_{H-F6}$=13.2 Hz; 1H; H-5); 8.64 (s; 1H; H-2); 14.9 (s wide; CO$_2$H).

$^{13}$C NMR (CDCl$_3$), in ppm: 46.10 (s; piperazino CH$_3$); 49.56 (d; $^4$J$_{C-F6}$=4.6 Hz; piperazino 2 CH$_2$); 54.65 (s; piperazino 2 CH$_2$); 105.62 (d; $^4$J$_{C-F6}$=3.8 Hz; CH-8); 108.62 (s; C-3); 112.49 (d; $^2$J$_{C-F6}$=23.7 Hz; CH-5); 117.98 (d; $^2$J$_{C-F4}$=23.6 Hz; aromatic CH-3' and CH-5'); 119.57 (s; C-4a); 129.20 (d; $^3$J$_{C-F6}$=9.2 Hz; aromatic CH-2' and CH-6'); 136.23 (d; $^4$J$_{C-F4}$=3.5 Hz; aromatic C-1'); 139.33 (s; C-8a); 146.01 (d; $^2$J$_{C-F6}$=10.7 Hz; C-7); 147.76 (s; CH-2); 153.68 (d; $^1$J$_{C-F6}$=250.5 Hz; C-6); 163.36 (d; $^1$J$_{C-F4}$=252.0 Hz; aromatic C-4'); 166.92 (s; CO$_2$H); 177.35 (s; CO)

IR (ATR) in cm$^{-1}$: 3050 (aromatic and aliphatic C—H stretching), 3000 to 2700 (O—H acid type dimer stretching and aromatic and aliphatic C—H stretching), 1733 (C=O acid type dimer stretching), 1627 (C=O conjugated ketone stretching and asymmetrical carboxylate ion O—C—O stretching), 1490 (aromatic C=C stretching), 1294 (aromatic C—F stretching).

Sarafloxacin: 1-(4-fluorophenyl)-6-fluoro-1,4-dihydro-7-(1-piperazinyl)-4-oxoquinoline-3-carboxylic acid; NR= [98105-99-8].

m.p.: 260-270° C.

$^1$H NMR (5% NaOD/D$_2$O) in ppm: 2.80 to 3.1 (m; 8H; piperazino 4 CH$_2$); 6.46 (d; $^3$J$_{H-F}$=7.0 Hz; 1H; H-8); 7.3 to 7.6 (m; aromatic 4H); 7.84 (d; $^4$J$_{H-F}$=13.8 Hz; 1H; H-5); 8.41 (s; 1H; H-2).

$^{13}$C NMR (5% NaOD/D$_2$O) in ppm: 42.04-48.18 (2 s; piperazino 4 CH$_2$); 104.63 (s; CH-8); 109.37 (d; $^2$J$_{C-F}$=23.7 Hz; CH-5); 115.19 (d; $^2$J$_{C-F}$=23.7 Hz; aromatic 2 CH-3' and 5'); 115.35 (s; C-3); 119.67 (d; $^3$J$_{C-F}$=6.9 Hz; C-4a); 127.15 (d; $^3$J$_{C-F}$=9.2 Hz; aromatic CH-2' and 6'); 134.36-136.27 (2 s; aromatic C-1' and C-8a); 142.44 (d; $^2$J$_{C-F}$=11.5 Hz; C-7); 144.82 (s; CH-2); 150.95 (d; $^1$J$_{C-F}$=246.6 Hz; C-6); 160.69 (d; $^1$J$_{C-F}$=246.7 Hz; aromatic C-4'); 170.17 (s; COOH); 173.39 (s; CO).

IR (ATR) in cm$^{-1}$: 3650 to 3200 (O—H bonded type dimer stretching and N—H secondary amine stretching), 3070 (aromatic and aliphatic C—H stretching), 3000 to 2800 and 2800 to 2200 (O—H acid type dimer stretching and aromatic and aliphatic C—H stretching), 1728 (C-0 acid type dimer stretching), 1619 (C=O conjugated ketone stretching and asymmetrical carboxylate ion O—C—O stretching), 1470 (aromatic C=C stretching), 1296 (aromatic C—F stretching), 925 (H—O out of plane deformation).

Pefloxacin: 1-ethyl-6-fluoro-1,4-dihydro-7-(4-methyl-1-piperazinyl)-4-oxoquinoline-3-carboxylic acid; NR= [70458-92-3].

m.p.: 266-272° C. [lit.: 270-2° C. Merck Index Ed 14$^{th}$, 7066].

$^1$H NMR (5% NaOD/D$_2$O), in ppm: 1.39 (t; $^3$J=6.8 Hz; 3H; ethyl CH$_3$); 2.33 (s; 3H; piperazino CH$_3$); 2.5 to 2.7 (m; 4H; piperazino 2 CH$_2$); 3.1 to 3.3 (m; 4H; piperazino 2 CH$_2$); 4.19 (pseudo q; 2H; ethyl CH$_2$); 6.82 (d; $^4$J$_{H-F}$=6.8 Hz; 1H; H-8); 7.71 (d; $^3$J$_{H-F}$=13.8 Hz; 1H; H-5); 8.36 (s; 1H; H-2).

$^{13}$C NMR (5% NaOD/D$_2$O) in ppm: 16.29 (s; ethyl CH$_3$); 47.23 (s; CH$_3$ piperazino); 51.57 (s; Ethyl CH$_2$); 52.0 (d; $^4$J$_{C-F6}$=3.8 Hz; piperazino 2 CH$_2$); 56.22 (s; piperazino 2 CH$_2$); 107.55 (s; CH-8); 114.28 (d; $^2$J$_{C-F6}$=22.9 Hz; CH-5); 119.19 (s; C-3); 124.97 (d; $^3$J$_{C-F6}$=9.5 Hz; C-4a); 138.88 (s; C-8a); 146.66 (d; $^2$J$_{C-F6}$=11.4 Hz; C-7); 149.53 (s; CH-2); 155.30 (d; $^1$J$_{C-F6}$=245.9 Hz; C-6); 174.91 (s; CO$_2$H); 177.66 (d; $^4$J$_{C-F6}$=2.3 Hz; CO).

IR (ATR) in cm$^{-1}$: 3060 (aromatic and aliphatic C—H stretching), 3000 to 2750 (O—H acid type dimer stretching and aromatic and aliphatic C—H stretching), 1736 (C=O acid type dimer stretching), 1625-1615 (C=O conjugated ketone stretching and asymmetrical carboxylate ion O—C—O stretching), 1475 (aromatic C=C stretching), 1256 (aromatic C—F stretching), 950 (H—O out of plane deformation).

Amifloxacin: 1-methylamino-6-fluoro-1,4-dihydro-7-(4-methyl-1-piperazinyl)-4-oxoquinoline-3-carboxylic acid; NR=[86393-37-5].

m.p.: 250-260° C.

$^1$H NMR (5% NaOD/D$_2$O) in ppm: 2.34 (s; 3H; piperazino CH$_3$); 2.55 to 2.85 (m; 4H; piperazino 2 CH$_2$); 2.87 (s; 3H; NCH$_3$); 3.1 to 3.3 (m; 4H; piperazino 2 CH$_2$); 7.34 (d; $^4$J$_{H-F6}$=6.8 Hz; 1H; H-8); 7.70 (d; $^3$J$_{H-F6}$=13.6 Hz; 1H; H-5); 8.53 (s; 1H; H-2).

$^{13}$C NMR (5% NaOD/D$_2$O) in ppm: 35.82 (s; NCH$_3$); 42.50 (s; piperazino CH$_3$); 47.34-51.47 (2 s; 4 piperazino CH$_2$); 102.51 (s; CH-8); 109.31 (d; $^2$J$_{C-F6}$=23.7

Hz; CH-5); 114.79 (s; C-3); 119.6 (d; $^3J_{C-F6}$=6.8 Hz; C-4a); 134.90 (s; C-8a); 142.24 (d; $^2J_{C-F6}$=10.6 Hz; C-7); 143.97 (s; CH-2); 150.75 (d; $^1J_{C-F6}$=246.6 Hz; C-6); 169.82 (s; CO$_2$H); 172.6 (d; $^4J_{C-F6}$=2.3 Hz; CO).

IR (ATR) in cm$^{-1}$: 3298 (N—H hydrazine secondary amine stretching), 3050 (aromatic and aliphatic C—H stretching), 3000 to 2700 (O—H acid type dimer stretching and aromatic and aliphatic C—H stretching), 1718 (C=O acid type dimer stretching), 1628-1611 (C=O conjugated ketone stretching and asymmetrical carboxylate ion O—C—O stretching), 1485 (aromatic C=C stretching), 1290 (aromatic C—F stretching), 965 (H—O out of plane deformation).

Enrofloxacin: 1-cyclopropyl-6-fluoro-1,4-dihydro-7-(4-ethyl-1-piperazinyl)-4-oxoquinoline-3-carboxylic acid; NR=[93106-60-6].

m.p.: 222-4° C. (lit.: 219-221° C., Merck Index 14th, 3592).

$^1$H NMR (CDCl$_3$) in ppm: 1.16 (t; $^3J$=7.4 Hz; 3H; ethyl CH$_3$); 1.16 to 1.24 (m; 2H; cyclopropyl CH$_2$); 1.30 to 1.45 (m; 2H; cyclopropyl CH$_2$); 2.52 (q; $^3J$=6.8 Hz; 2H; Ethyl CH$_2$); 2.65 to 2.75 (m; 4H; piperazino 2 CH$_2$); 3.35 to 3.42 (m; 4H; piperazino 2 CH$_2$); 3.56 (m; 1H; cyclopropyl CH); 7.35 (d; $^4J_{H-F6}$=7.4 Hz; 1H; H-8); 7.99 (d; $J_{H-F6}$=13.2 Hz; 1H; H-5); 8.75 (s; 1H; H-2).

$^{13}$C NMR (CDCl$_3$), in ppm: 8.28 (s; cyclopropyl 2 CH$_2$); 12.03 (s; ethyl CH$_3$); 35.41 (s; cyclopropyl CH); 49.79-49.80-52.34-52.51 (4 s; piperazino 4 CH$_2$); 104.88 (d; $^3J_{C-F6}$=3.8 Hz; CH-8); 108.01 (s; C-3); 112.26 (d; $^2J_{C-F6}$=23.7 Hz; CH-5); 119.63 (d; $^3J_{C-F6}$=8.4 Hz; C-4a); 139.17 (s; C-8a); 146.04 (d; $^2J_{C-F6}$=10.7 Hz; C-7); 147.42 (s; CH-2); 153.73 (d, $^1J_{C-F6}$=250.4 Hz; C-6); 167.13 (s; CO$_2$H); 177.09 (d; $^4J_{C-F6}$=3.0 Hz; CO).

IR (ATR) in cm$^{-1}$: 3500 to 3100 (O—H bonded type dimer stretching), 3080 (aromatic and aliphatic C—H stretching), 3000 to 2700 (O—H acid type dimer stretching and aromatic and aliphatic C—H stretching), 1735 (C=O acid type dimer stretching), 1626 (C=O conjugated ketone stretching and asymmetrical carboxylate ion O—C—O stretching), 1464 (aromatic C=C stretching), 1291 (aromatic C—F stretching), 955 (H—O out of plane deformation).

Ciprofloxacin: 1-cyclopropyl-6-fluoro-1,4-dihydro-7-(1-piperazinyl)-4-oxoquinoline-3-carboxylic acid; NR=[85721-33-1].

m.p.: 260-5° C. [lit: 255-7° C., decomposition; Merck Index 14th, 2314].

$^1$H NMR (5% NaOD/D$_2$O) in ppm: 0.95 to 1.1 (m; 2H; cyclopropyl CH$_2$); 1.2 to 1.4 (m; 2H; cyclopropyl CH$_2$); 2.9 to 3.15 (m; 4H; piperazino 2 CH$_2$); 3.15 to 3.25 (m; 4H; piperazino 2 CH$_2$); 3.4 to 3.6 (m; 1H; cyclopropyl CH); 7.39 (d; $^4J_{H-F}$=7.0 Hz; 1H; H-8); 7.69 (d; $^3J_{H-F}$=13.6 Hz; 1H; H-5); 8.45 (s; 1H; H-2).

$^{13}$C NMR (5% NaOD/D$_2$O) in ppm: 5.32 (s; cyclopropyl 2 CH$_2$); 32.63 (s; cyclopropyl CH); 42.19 (s; piperazino 2 CH$_2$); 48.55 (d; $^4J_{C-F6}$=3.8 Hz; piperazino 2 CH$_2$); 104.19 (s; CH-8); 109.27 (d; $^2J_{C-F6}$=23.6 Hz; CH-5); 114.27 (s; C-3); 119.84 (d; $^2J_{C-F6}$=7.6 Hz; C-4a); 136.27 (s; C-8a); 142.36 (d; $^2J_{C-F6}$=10.7 Hz; C-7); 144.98 (s; CH-2); 151.02 (d; $^1J_{C-F6}$=245.9 Hz; C-6); 170.36 (s; CO$_2$H); 173.38 (s; CO).

IR (ATR) in cm$^{-1}$: 3600 to 3200 (O—H bonded type dimer stretching and N—H secondary amine stretching), 3100 to 2500 (O—H acid type dimer stretching and aromatic and aliphatic C—H stretching), 1615 (C=O conjugated ketone stretching and asymmetrical carboxylate ion O—C—O stretching), 1478 (aromatic C=C stretching), 1291 (aromatic C—F stretching), 941 (H—O out of plane deformation).

1-cyclopropyl-6-fluoro-1,4-dihydro-4-oxo-7-(1-piperazinyl)-1,8-naphthyridin-3-carboxylic acid; NR=[99735-41-8].

m.p.: 266° C. [Lit.: 274-6° C.; EP153163 (1985)]

$^1$H NMR (5% NaOD/D$_2$O) in ppm: 1.1 to 1.3 (m; 4H; 2 CH$_2$ cyclo-propyl); 2.8 à 3.0 (m; 4H; piperazino 2 CH$_2$); 3.38 (m; 1H; cyclopropyl CH); 3.6 to 3.8 (m; 4H; piperazino 2 CH$_2$); 7.69 (d; $^3J$=14.2 Hz; 1H; H-5); 8.36 (s; 1H; H-2).

$^{13}$C NMR (5% NaOD/D$_2$O) in ppm: 9.28 (s; cyclopropyl 2 CH$_2$); 36.36 (s; cyclopropyl CH); 47.20 (s; piperazino 2 CH$_2$); 49.90 (d; $^4J_{C-F6}$=7.7 Hz; piperazino 2 CH$_2$); 116.65 (s; C-3 or C-4a); 119.47 (s; C-4a or C-3); 122.16 (d; $^2J_{C-F6}$=21.4 Hz; CH-5); 148.27 (s; C-7); 148.49 (s; CH-2); 148.99 (d; $^1J_{C-F6}$=250.5 Hz; C-6); 151.63 (s; C-8a); 174.51 (s; CO$_2$H); 178.09 (s; CO).

IR (ATR) in cm$^{-1}$: 1723 (C=O acid type dimer stretching), 1629 (C=O conjugated ketone stretching and asymmetrical carboxylate ion O—C—O stretching), 1438 (aromatic C=C stretching), 1262 (aromatic C—F stretching), 952 (H—O out of plane deformation).

1-(2,4-difluorophenyl)-6-fluoro-1,4-dihydro-4-oxo-7-(1-piperazinyl)-1,8-naphthyridine-3-carboxylic acid; NR=[100490-19-5].

m.p.: 231° C. [lit: 274-6° C.; EP153163 (1985).

$^1$H NMR (5% NaOD/D$_2$O) in ppm: 2.5 to 2.8 (m; 4H; piperazino 2 CH$_2$), 3.2 to 3.6 (m; 4H; piperazino 2 CH$_2$); 7.05 to 7.3 (m; 2H; 2 CH of the phenyl ring); 7.3 to 7.5 (m; 1H; phenyl ring CH); 7.82 (d; $^3J$=13.6 Hz; 1H; H-5); 8.38 (s; 1H; H-2).

$^{13}$C NMR (DMSO-d6) in ppm: 45.31 (s; piperazino 2 CH$_2$); 48.03 (d; $^4J_{C-F6}$=6.9 Hz, piperazino 2 CH$_2$); 104.75 (dd; $^2J_{C-F}$=26.7 Hz and 27.5 Hz; CH-3'); 109.14 (s; C-3); 111.61 (d; $^3J_{C-F6}$=3.1 Hz; C-4a); 112.25 (dd; $^2J_{C-F4}$=22.9 Hz and $^4J_{C-F2'}$=3.1 Hz; aromatic CH-5'); 119.32 (d; $^2J_{C-F6}$=22.9 Hz; CH-5); 124.03 (dd; $^2J_{C-F2'}$=13.0 Hz and $^4J_{C-F4'}$=3.8 Hz; aromatic C-1'); 130.87 (d; $^3J_{C-F}$=10.7 Hz; aromatic CH-6'); 145.71 (s; C-8a); 146.89 (d; $^1J_{C-F6}$=258.1 Hz; C-6); 148.03 (s; CH-2); 149.74 (d; $^2J_{C-F6}$=9.2 Hz; C-7); 157.26 (dd; $^1J_{C-F}$=251.2 Hz and $^3J_{C-F}$=13.8 Hz; aromatic C-2' or C-4'); 162.58 (dd; $^1J_{C-F}$=248.2 Hz and $^3J_{C-F}$=11.8 Hz; aromatic C-4' or C-2'); 165.36 (s; CO$_2$H); 176.89 (s; CO).

IR (ATR) in cm$^{-1}$: 3600 to 3200 (O—H bonded type dimer stretching and N—H secondary amine stretching), 3100 to 2200 (O—H acid type dimer stretching and aromatic and aliphatic C—H stretching), 1626 (C=O conjugated ketone stretching), 1509 (asymmetrical carboxylate ion O—C—O stretching and N—H deformation vibration), 1442 (aromatic C=C stretching), 1269 (aromatic C—F stretching).

In the case of condensation of certain primary amines with compounds of type II, the method of preparation can be modified according to the procedure which has been used and is described below.

Example 2

Method of preparation of 1-ethyl-6,8-difluoro-1,4-dihydro-7-(benzylamino)-4-oxoquinoline-3-carboxylic acid

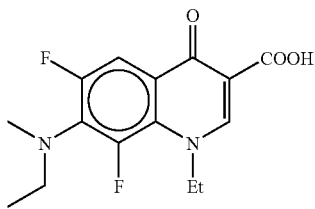

In a 50 ml erlenmeyer flask, suspend 3 g of 1-ethyl-6,7,8-trifluoro-1,4-dihydro-4-oxoquinoline-3-ethyl carboxylate and 3.1 g of potassium carbonate in 18 ml of softened water. Heat the reaction medium to 90-95° C. all together for 24 hours until totally dissolved then add 3.2 g of benzylamine and continue heating for a further 8 hours, monitoring the development of the reaction by TLC. When the reaction is ended, cool the reaction medium to ambient temperature and adjust the pH to approximately 7.5 by addition of 15% hydrochloric acid. Filter the precipitate formed on a frit and rinse successively with 6 ml softened water then with 6 ml of acetone. The product obtained is purified by acid-base alternation then oven dried at 50° C. 2.2 g of white crystals are obtained. (Yield ~56%).

1-ethyl-6,8-difluoro-1,4-dihydro-7-(benzylamino)-4-oxoquinoline-3-carboxylic acid; $C_{19}H_{16}F_2N_2O_3$=358.34.

m.p.: 200° C.

$^1$H NMR (CDCl$_3$) in ppm: 1.50 (t; $^3J$=6.8 Hz; 3H; ethyl CH$_3$); 4.35 to 4.6 (m; 2H; ethyl CH$_2$); 4.73 (s; 2H; benzyl CH$_2$); 7.36 (s; phenyl ring 5H); 7.94 (dd; $^3J_{H-F}$=12.0 Hz and $^5J_{H-F}$=2.0 Hz; 1H; H-5); 8.55 (s; 1H; H-2); 14.9 (s wide; CO$_2$H).

$^{13}$C NMR (5% NaOD/D$_2$O) in ppm: 17.90 (s; ethyl CH$_3$); 51.17 (s; benzyl CH$_2$); 55.55 (s wide; Ethyl CH$_2$); 109.41 (d; $^2J_{C-F6}$~20.5 Hz; C-5); 117.92 (s; C-3); 121.36 (d; $^2J_{C-F8}$~6.9 Hz; C-8a); 128.42 (d; $^3J_{C-F6}$~5.0 Hz; C-4a); 129.51-129.84-130.81 (3 s; phenyl ring 5 CH); 132.47 (pseudo t; $^2J_{C-F}$=13.8 and 14.5 Hz; C-7); 141.93 (dd; $^1J_{C-F8}$~240 Hz and $^3J_{C-F6}$~6.5 Hz; C-8); 142.30 (s; phenyl ring C-1'); 151.98 (dd; $^1J_{C-F6}$~241.0 Hz and $^3J_{C-F8}$~8.0 Hz; C-6); 152.15 (s; CH-2); 174.27 (s; CO$_2$H); 176.63 (s; CO).

IR (ATR) in cm$^{-1}$ 3600 to 3200 (O—H bonded type dimer stretching and N—H secondary amine stretching), 3160 to 2850 (acid type dimer stretching and aromatic and aliphatic C—H stretching), 1708 (C=O acid type dimer stretching), 1633 and 1613 (C=O conjugated ketone stretching and asymmetrical carboxylate ion O—C—O stretching), 1484 (aromatic C=C stretching).

By way of examples, the following compounds are prepared according to the mode of operation of Example 2:

1-ethyl-6,8-difluoro-1,4-dihydro-7-(phenethylamino)-4-oxoquinoline-3-carboxylic acid hydrochloride; $C_{20}H_{18}F_2N_2O_3$; HCl=408.83 m.p.: 160.5° C.

$^1$H NMR (CDCl$_3$) in ppm: 1.54 (dt; J=7.0 and 1.2 Hz; 3H; ethyl CH$_3$); 2.96 (t; $^3J$=7 Hz; 2H; phenethyl CH$_2$); 3.83 (tt; J=7.0 and 2.0 Hz; 2H; phenethyl CH$_2$); 4.43 (dq; J=7.0 and 3.1 Hz; 2H, Ethyl CH$_2$); 7.15 to 7.35 (m; aromatic 5H); 7.92 (dd; $^3J_{H-F}$=12.2 Hz and J$_{H-F}$=1.9 Hz; 1H; H-5); 8.56 (s; 1H; H-2).

$^{13}$C NMR (DMSO-d$_6$) in ppm: 15.84 (d; $^5J_{C-F8}$=5.4 Hz; ethyl CH$_3$); 36.79-46.12 (2 s; phenethyl 2 CH$_2$); 53.44 (d; $^4J_{C-F8}$=16.0 Hz; Ethyl CH$_2$); 106.37 (s; C-3); 106.50 (d; $^2J_{C-F6}$=22.1 Hz; CH-5); 114.33 (d; $J_{C-F}$=7.6 Hz; C-8a); 126.21 (s; phenyl ring CH-4'); 126.87 (d; $J_{C-F}$=5.4 Hz; C-4a); 128.36-128.70 (2 s; phenyl ring 4 CH-3' and 5'); 132.27 (pseudo t; $^2J_{C-F}$=13.7 and 14.6 Hz; C-7); 138.90 (s; phenyl ring C-1'); 139.04 (dd; $^1J_{C-F8}$=240.5 Hz and $^3J_{C-F6}$=7.6 Hz; C-8); 150.27 (s; CH-2); 149.83 (dd; $^1J_{C-F6}$=244.4 Hz and $^3J_{C-F8}$=7.7 Hz; C-6); 165.82 (s; COOH); 175.26 (s; CO).

IR (cm$^{-1}$): 3341 (O—H bonded type dimer stretching), 3200 to 2800 (O—H bonded type dimer stretching and aromatic and aliphatic C—H stretching), 1717 (C=O acid type dimer stretching), 1632-1614 (C=O conjugated ketone stretching and asymmetrical carboxylate ion O—C—O stretching), 1463 (aromatic C=C stretching), 1274 (aromatic C—F stretching).

Example 3

The following compounds were prepared according to the mode of operation of Example 1.

6,8-difluoro-1,4-dihydro-1-(2-hydroxyethyl)-7-(4-methyl-1-piperazinyl)-4-oxoquinoline-3-carboxylic acid;

m.p.: >300° C.

$^1$H NMR (DMSO-d$_6$) in ppm: 2.78 (s; 3H; piperazino CH$_3$); 3.0 to 3.5 (m; 4H; piperazino 2 CH$_2$); 3.5 to 3.7 (m; 4H; piperazino 2 CH$_2$); 3.79 (m; 2H; hydroxyethyl CH$_2$—N); 4.64 (m; 2H; hydroxyethyl CH$_2$); 5.13 (s wide; 1H; OH); 7.89 (d; $^3J_{H-F6}$=11.8 Hz; 1H; H-5); 8.76 (s; 1H; H-2); 11.6 (s wide; 1H; COOH).

$^{13}$C NMR (DMSO-d$_6$) in ppm: 42.41 (s; piperazino CH$_3$); 47.40-52.92 (2 s; piperazino CH$_2$ and hydroxyethyl CH$_2$); 59.24 (s; hydroxyethyl CH$_2$); 60.66 (d; $^4J_{C-F}$=13.8 Hz; piperazino CH$_2$); 106.35 (s; C-3); 107.07 (d; $^2J_{C-F}$=23.7 Hz; CH-5); 121.48 (pseudo d; C-8a); 127.28 (pseudo d; C-4a); 132.49 (s; C-7); 146.55 (d; $^1J_{C-F8}$=244.0 Hz; C-8); 152.68 (s; CH-2); 154.44 (d; $^1J_{C-F6}$=254.3 Hz; C-6); 165.63 (s; COOH); 175.71 (s; CO).

IR (ATR) in cm$^{-1}$: 3600 to 3000 (O—H bonded type dimer stretching), 3064 (aromatic and aliphatic C—H stretching), 3000 to 2800 (aromatic and aliphatic C—H stretching), 2700 to 2400 (O—H bonded acid type dimer stretching), 1732 (C=O acid type dimer stretching), 1625-1604 (C=O conjugated ketone stretching and asymmetrical carboxylate ion O—C—O stretching), 1476 (aromatic C=C stretching), 1286 (aromatic C—F stretching), 807 (isolated aromatic C—H stretching).

1-ethyl-6,8-difluoro-1,4-dihydro-7-(4-methyl-1-piperidinyl)-4-oxoquinoline-3-carboxylic acid;

m.p.: 234° C.

$^1$H NMR (CDCl$_3$) in ppm: 1.02 (d; $^3J$=5.8 Hz; 3H; piperidinyl CH$_3$); 1.25 to 1.55 (m; 2H; piperidinyl CH$_2$); 1.57 (td; $^3J$=7.0 Hz and $^6J_{H-F8}$=0.8 Hz; 3H; ethyl CH$_3$); 1.65 to 1.85 (pseudo d; J=12.0 Hz; 2H; piperidinyl CH$_2$); 3.23 (pseudo t; J=11.5 Hz; 2H; piperidinyl CH$_2$); 3.35 to 3.55 (pseudo d; J=12.2 Hz; 2H; piperidinyl CH$_2$); 4.48 (dq; $^3J$=7.0 Hz and $^5J_{H-F8}$=3.2 Hz; 2H; ethyl CH$_2$); 7.91 (dd; $^3J_{H-F6}$~12.2 Hz and $^5J_{H-F8}$~2 Hz; 1H; H-5); 8.60 (s; 1H; H-2).

$^{13}$C NMR (CDCl$_3$) in ppm: 16.42 (d; $^5J_{C-F8}$=5.4 Hz; ethyl CH$_3$); 22.08 (s; piperidinyl CH$_3$); 30.62 (s; piperidinyl CH); 34.86 (s; piperidinyl 2 CH$_2$); 51.72 (pseudo t;

J=4.0 Hz; piperidinyl 2 CH$_2$); 54.73 (d; $^4J_{C-F8}$=16.8 Hz; ethyl CH$_2$); 107.82 (s; C-3); 108.06 (dd; $^2J_{C-F6}$=23.7 Hz and $^4J_{C-F8}$~3.5 Hz; CH-5); 120.50 (d; $^2J_{C-F8}$=9.2 Hz; C-8a); 127.27 (d; $^3J_{C-F6}$=6.9 Hz; C-4a); 135.46 (pseudo t; $^2J_{C-F}$~13.8 Hz; C-7); 145.75 (dd; $^1J_{C-F8}$~246.6 Hz and $^3J_{C-F6}$~1.5 Hz; C-8); 149.95 (s; CH-2); 155.33 (dd; $^1J_{C-F6}$~249.7 Hz and $^3J_{C-F8}$~1.3 Hz; C-6); 166.84 (s; COOH); 176.28 (s; CO).

IR (ATR) in cm$^{-1}$: 3053 (aromatic and aliphatic C—H stretching), 3000 to 2600 (O—H bonded acid type dimer stretching and aromatic and aliphatic C—H stretching), 1717 (C=O acid type dimer stretching), 1620 (C=O conjugated ketone stretching and asymmetrical carboxylate ion O—C—O stretching), 1470 (aromatic C=C stretching), 1279 (aromatic C—F stretching), 926 (H—O out of plane deformation), 808 (isolated aromatic C—H stretching).

1-ethyl-6,8-difluoro-1,4-dihydro-7-(3,4-dihydro-2(1H)-isoquinolinyl)-4-oxo-quinoline-3-carboxylic acid; NR=[138276-64-9]

m.p.: 226° C.

$^1$H NMR (CDCl$_3$) in ppm: 1.58 (dt; $^3J$=7.4 Hz and $^6J_{H-F8}$=1.6 Hz; 3H; ethyl CH$_3$); 3.07 (t; $^3J$=5.8 Hz; 2H; tetrahydroisoquinolinyl CH$_2$); 3.68 (t; $^3J$=5.8 Hz; 2H; tetrahydroisoquinolinyl CH$_2$—N); 4.46 (dq; $^3J$=7.4 Hz and $^5J_{H-F8}$=3.0 Hz; 2H; ethyl CH$_2$); 4.62 (s; 2H; tetrahydroisoquinolinyl CH$_2$—N); 7.05 to 7.15 (m; 1H; aromatic tetrahydroisoquinolinyl H); 7.15 to 7.30 (m; 3H; aromatic tetrahydroisoquinolinyl 3H); 7.97 (dd; $^3J_{H-F8}$~12.0 Hz and $^5J_{H-F6}$~2.0 Hz; 1H; H-5); 8.61 (s; 1H; H-2).

$^{13}$C NMR (CDCl$_3$) in ppm: 16.47 (d; $^5J_{C-F8}$=5.3 Hz; ethyl CH$_3$); 29.62 (s; tetrahydroisoquinolinyl CH$_2$); 49.35 (pseudo t; $^4J$=3.8 Hz; tetrahydroisoquinolinyl CH$_2$—N); 52.67 (s; tetrahydroisoquinolinyl CH$_2$—N); 54.74 (d; $^4J_{C-F8}$=16.8 Hz; ethyl CH$_2$); 108.11 (s; C-3); 108.44 (dd; $^4J_{C-F8}$~3.0 Hz and $^2J_{C-F6}$~23.7 Hz; CH-5); 121.02 (d; $^2J_{C-F8}$~8.0 Hz; C-8a); 126.10-126.24-126.71 (3 s; aromatic tetrahydroisoquinolinyl CH); 127.31 (d; $^3J_{C-F6}$=7.0 Hz; C-4a); 129.32 (s; aromatic tetrahydroisoquinolinyl CH); 133.83-134.09 (2 s, quaternary tetrahydroisoquinolinyl 2 C); 134.58 (pseudo t; $^2J_{C-F}$~14.5 Hz; C-7); 145.77 (dd; $^1J_{C-F8}$=247.4 Hz and $^3J_{C-F6}$~6.1 Hz; C-8); 150.11 (s; CH-2); 155.16 (dd; $^1J_{C-F6}$~249.7 Hz and $^3J_{C-F8}$~6.5 Hz; C-6); 166.77 (s; COOH); 176.36 (s; CO).

IR (ATR) in cm$^{-1}$: 3100 to 2700 (aromatic and aliphatic C—H stretching), 2700 à 2400 (O—H bonded acid type dimer stretching), 1721 (C=O acid type dimer stretching), 1623 (C=O conjugated ketone stretching and asymmetrical carboxylate ion O—C—O stretching), 1468 (aromatic C=C stretching), 1276 (aromatic C—F stretching), 949 (H—O out of plane deformation); 803 (isolated aromatic C—H stretching).

1-ethyl-6,8-difluoro-1,4-dihydro-7-(thiomorpholinyl)-4-oxoquinoline-3-carboxylic acid; NR=[93509-84-3].

m.p.: 287° C. [lit.: >300° C.; U.S. Pat. No. 4,473,568 (1984)]

$^1$H NMR (CDCl$_3$) in ppm: 1.57 (dt; $^3J$=7.2 Hz and $^6J_{H-F8}$~1.0 Hz; 3H; ethyl CH$_3$); 2.7 to 2.9 (m; 4H; thiomorpholino CH$_2$); 3.55 to 3.7 (m; 4H; thiomorpholino CH$_2$); 4.4 to 4.6 (dq; $^3J$=7.2 Hz and $^5J_{H-F8}$=3.4 Hz; 2H; ethyl CH$_2$); 7.98 (dd; $^3J_{H-F6}$=10.8 Hz and $^5J_{H-F8}$=2.0 Hz; 1H; H-5); 8.62 (s; 1H; H-2); 14.63 (s; 1H; COOH).

$^{13}$C NMR (CDCl$_3$) in ppm: 16.51 (d; $^5J_{C-F8}$~5.4 Hz; ethyl CH$_3$); 28.26 (s; thiomorpholino 2 CH$_2$—S); 53.52 (pseudo t; J=3.8 Hz; thiomorpholino CH$_2$—N); 54.74 (d; $^4J_{C-F8}$=16.8 Hz; ethyl CH$_2$); 108.36 (s; C-3); 108.68 (d; $^2J_{C-F6}$=22.9 Hz; CH-5); 146.47 (d; $^1J_{C-F8}$=247.6 Hz; C-8); 150.21 (s; CH-2); 155.48 (d; $^1J_{C-F6}$=244.4 Hz; C-6); 166.71 (s; COOH); 176.45 (s; CO).

IR (ATR) in cm$^{-1}$: 3046 (aromatic and aliphatic C—H stretching), 3100 to 2700 and 2700 to 2400 (O—H bonded acid type dimer stretching and aromatic and aliphatic C—H stretching), 1710 (C=O acid type dimer stretching), 1619 (C=O conjugated ketone stretching and asymmetrical carboxylate ion O—C—O stretching), 1466 (aromatic C=C stretching), 1289 (aromatic C—F stretching), 957 (H—O out of plane deformation); 804 (isolated aromatic C—H stretching).

8-chloro-1-cyclopropyl-6-fluoro-1,4-dihydro-7-(4-methyl-1-piperazinyl)-4-oxoquinoline-3-carboxylic acid; NR=[99696-26-1]

m.p.: 279° C.

$^1$H NMR (4% NaOD/D$_2$O) in ppm: 0.65 to 0.90 (m; 2H; cyclopropyl); 1.0 to 1.3 (m; 2H; cyclopropyl); 2.28 (s; 3H; piperazino CH$_3$); 2.4 to 2.7 (m; 4H; piperazino 2 CH$_2$); 3.1 to 3.4 (m; 4H; piperazino 2 CH$_2$); 4.1 (m; 1H; cyclopropyl CH); 7.69 (d; $^3J_{H-F6}$=12.6 Hz; 1H; H-5); 8.57 (s; 1H; H-2).

$^{13}$C NMR (4% NaOD/D$_2$O) in ppm: 13.24 (s; cyclopropyl 2 CH$_2$); 42.73 (s; cyclopropyl CH); 47.61 (s; piperazino CH$_3$); 52.82 (s; piperazino 2 CH$_2$); 57.17 (s; piperazino 2 CH$_2$); 113.60 (d; $^2J_{C-F6}$=23.7 Hz; CH-5); 119.00 (s; C-3); 121.22 (d; J$_{C-F6}$=5.4 Hz; C-8a); 127.35 (d; J$_{C-F6}$=6.9 Hz; C-4a); 139.85 (s; C-8); 144.98 (d; $^2J_{C-F6}$=14.5 Hz; C-7); 154.14 (s; CH-2); 157.58 (d; $^1J_{C-F6}$=248.2 Hz; C-6); 173.88 (s; COOH); 177.53 (s; CO).

IR (ATR) in cm$^{-1}$: 3600 to 3100 (O—H bonded type dimer stretching), 2700 to 2300 (O—H bonded type dimer stretching and aromatic and aliphatic C—H stretching) 1716 (C=O acid type dimer stretching), 1613 (C=O conjugated ketone stretching and asymmetrical carboxylate ion O—C—O stretching), 1458-1448 (aromatic C=C stretching), 1280 (aromatic C—F stretching), 950 (H—O out of plane deformation), 806 (isolated aromatic C—H stretching).

8-chloro-1-cyclopropyl-6-fluoro-1,4-dihydro-7-(4-ethyl-1-piperazinyl)-4-oxo-quinoline-3-carboxylic acid; NR=[116020-28-1].

m.p.: 200° C.

$^1$H NMR (CDCl$_3$) in ppm: 0.9 to 1.05 (m; 2H; cyclopropyl); 1.16 (t; $^3J$=7 Hz; 3H; ethyl CH$_3$); 1.2 to 1.4 (pseudo q; 2H; cyclopropyl); 2.54 (q; $^3J$=7 Hz; 2H; ethyl CH$_2$); 2.55 to 2.75 (m; 4H; piperazino 2 CH$_2$); 3.35 to 3.55 (m; 4H; piperazino 2 CH$_2$); 4.36 (m; 1H; cyclopropyl CH); 7.98 (d; $^3J_{H-F6}$=12.0 Hz; 1H; H-5); 8.89 (s; 1H; H-2); 13.5 (s wide; 1H; COOH).

$^{13}$C NMR (CDCl$_3$) in ppm: 11.44 (s; cyclopropyl 2 CH$_2$); 11.97 (s; ethyl CH$_3$); 41.32 (s; cyclopropyl CH); 51.25 (d; $^4J_{C-F6}$=4.6 Hz; piperazino 2 CH$_2$); 52.59 (s; ethyl CH$_2$); 53.26 (s; piperazino 2 CH$_2$); 108.60 (s; C-3); 111.66 (d; $^2J_{C-F6}$=23.7 Hz; CH-5); 119.39 (d; $^4J_{C-F6}$=5.5 Hz; C-8a); 123.33 (d; $^3J_{C-F6}$=8.4 Hz; C-4a); 138.12 (s; C-8); 144.68 (d; $^2J_{C-F6}$=13.8 Hz; C-7); 151.95 (s; CH-2); 156.27 (d; J$_{C-F6}$=252.0 Hz; C-6); 166.14 (s; COOH); 176.81 (d; $^4J_{C-F6}$=3.0 Hz; CO).

IR (ATR) in cm$^{-1}$: 3088 (aromatic and aliphatic C—H stretching), 3000 to 2770 (O—H acid type dimer stretching and aromatic and aliphatic C—H stretching), 1723 (C=O acid type dimer stretching), 1614-1601 (C=O conjugated ketone stretching and asymmetrical carboxylate ion O—C—O stretching), 1429 (aromatic C═C stretching); 1257 (aromatic C—F stretching), 806 (isolated aromatic C—H stretching).

The invention claimed is:
1. Method of preparation of a compound of formula (I):

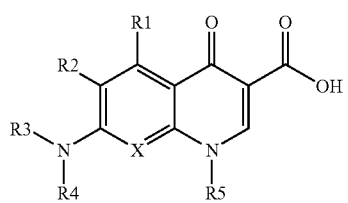

or an acidic or basic addition salt thereof,
wherein:
$R_1$ represents a group chosen from amongst hydrogen, alkyl or NRR';
$R_2$ represents a fluorine atom;
$R_3$, $R_4$, which are identical or different,
independently represent a hydrogen, alkyl, cycloalkyl, hydroxyl, aralkyl group, the said alkyl, cycloalkyl, aralkyl groups being capable of being optionally substituted by one or several hydroxyl groups, or NRR';
or
form together with the nitrogen atom to which they are attached a heterocyclyl group optionally substituted by one or several groups chosen from amongst alkyl, hydroxyl, alkoxy, —C(═O)alkyl, NRR', ═NOR, aralkyl, aryl, heteroaryl,
the said alkyl, aryl and heteroaryl groups being capable of being optionally substituted by one or several groups chosen from amongst alkyl, halogen, perfluoroalkyl, alkoxy, NRR';
$R_5$ represents a group chosen from amongst hydrogen, alkyl, cycloalkyl, Aryl, NR(CHO) or NRR', the said alkyl and aryl groups being capable of being optionally substituted by one or several groups chosen from amongst halogen or hydroxyl;
X represents a group $CR_8$ or a nitrogen atom;
$R_8$ represents a group chosen from amongst hydrogen, halogen, alkyl or alkoxy, or forms with $R_5$ a heterocyclyl group, optionally substituted by one or several alkyl groups;
R, R', which are identical or different, independently represent a hydrogen or alkyl group;
the said method comprising:
i) the reaction of a compound of formula (II)

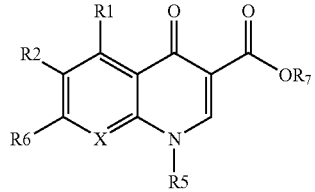

wherein
$R_1$, $R_2$, $R_5$ and X are as defined above,
$R_6$ represents a halogen atom,
$R_7$ represents an alkyl group,
with an amine of formula $R_3R_4NH$ in water in the presence of a mineral base,
thereby obtaining a basic addition salt of a compound of formula (I);
optionally the acidification of the obtained reaction medium, thereby obtaining the compound of formula (I) or an acidic addition salt thereof; and optionally
ii) the recovery of the obtained compound of formula (I) obtained or the acidic or basic addition salt thereof.

2. Method according to claim 1, wherein the amine $R_3R_4NH$ represents 1 to 5 molar equivalents with respect to the compound of formula (II).

3. Method according to claim 1, wherein the mineral base is an alkali metal carbonate or hydrogen carbonate.

4. Method according to claim 3, wherein the mineral base is chosen from amongst $K_2CO_3$, $KHCO_3$, $Na_2CO_3$, or $NaHCO_3$.

5. Method according to claim 1, wherein $R_6$ represents a fluorine or chlorine atom.

6. Method according to claim 1, wherein $R_3$ and $R_4$ together form a heterocyclyl group.

7. Method according to claim 6, wherein $R_3$ and $R_4$ form a piperazinyl group.

8. Method according to claim 1, wherein the compound of formula (I) is lomefloxacin.

9. Method according to claim 1, wherein the compound of formula (I) obtained is reacted with a hydrochloric acid solution.

10. Method according to claim 1, wherein the acidification is performed by adding hydrochloric acid to adjust the pH to approximately 7.5, thereby obtaining the compound of formula (I).

* * * * *